United States Patent
Childers et al.

(10) Patent No.: US 10,293,091 B2
(45) Date of Patent: May 21, 2019

(54) DIALYSIS SYSTEM HAVING AN AUTOCONNECTION MECHANISM

(71) Applicants: Baxter International Inc., Deerfield, IL (US); Baxter Healthcare S.A., Glattpark (Opfikon) (CH)

(72) Inventors: Robert W. Childers, Trinity, FL (US); Patrick Lee, Long Grove, IL (US); Andrey Kopychev, Clearwater, FL (US); Douglas Reitz, Green Oaks, IL (US); Rodolfo Roger, Clearwater, FL (US); John E. Steck, Round Lake, IL (US)

(73) Assignees: BAXTER INTERNATIONAL INC., Deerfield, IL (US); BAXTER HEALTHCARE S.A., Glattpark (Opfikon) (CH)

( * ) Notice: Subject to any disclaimer, the term of this patent is extended or adjusted under 35 U.S.C. 154(b) by 552 days.

(21) Appl. No.: 15/002,535

(22) Filed: Jan. 21, 2016

(65) Prior Publication Data

US 2016/0136345 A1    May 19, 2016

Related U.S. Application Data

(63) Continuation of application No. 13/493,743, filed on Jun. 11, 2012, now Pat. No. 9,242,034, which is a
(Continued)

(51) Int. Cl.
*A61M 1/14*    (2006.01)
*A61M 1/16*    (2006.01)
(Continued)

(52) U.S. Cl.
CPC ............ *A61M 1/14* (2013.01); *A61M 1/1601* (2014.02); *A61M 1/1621* (2014.02);
(Continued)

(58) Field of Classification Search
CPC ........ A61M 1/14; A61M 1/1621; A61M 1/28; A61M 1/285; A61M 5/162; A61M 5/1626;
(Continued)

(56) References Cited

U.S. PATENT DOCUMENTS 1,896,379 A    2/1933    Ross
2,145,196 A    1/1939    Orrick
(Continued)

FOREIGN PATENT DOCUMENTS

DE    1936245    4/1966
DE    3210148    9/1983
(Continued)

OTHER PUBLICATIONS

Mexican Office Action dated Feb. 1, 2017, corresponding to Mexican Patent Application No. MX/a/2014/011379. 4 pages.
(Continued)

*Primary Examiner* — Andrew M Gilbert
(74) *Attorney, Agent, or Firm* — K&L Gates LLP

(57) ABSTRACT

A dialysis system including a disposable fluid pumping cassette including at least one flexible membrane attached to a housing and at least one port extending from the housing, the at least one port including a spike; at least one dialysis fluid supply in fluid communication with at least one tubing and tubing connector; an autoconnection device including a shuttle for moving the at least one tubing and tubing connector towards the spike of the at least one port, the autoconnection device including at least one lead screw in mechanical communication with the shuttle, a motor and power transmission equipment to transmit power from the motor to the at least one lead screw; and a controller programmed to operate the motor to move the at least one
(Continued)

tubing and tubing connector towards the spike of the at least one port of the disposable fluid pumping cassette.

16 Claims, 27 Drawing Sheets

Related U.S. Application Data continuation of application No. 11/773,522, filed on Jul. 5, 2007, now Pat. No. 8,496,609.

(51) Int. Cl.
*A61M 5/162* (2006.01)
*A61M 39/16* (2006.01)

(52) U.S. Cl.
CPC ........... *A61M 5/162* (2013.01); *A61M 5/1626* (2013.01); *A61M 39/165* (2013.01); *A61M 2205/12* (2013.01); *A61M 2205/128* (2013.01); *Y10T 29/49826* (2015.01)

(58) Field of Classification Search
CPC ........ A61M 2205/12; A61M 2205/121; A61M 39/165
See application file for complete search history.

(56) References Cited

U.S. PATENT DOCUMENTS

| | | | |
|---|---|---|---|
| 2,249,473 A | 7/1941 | Jackson et al. | |
| 3,227,877 A | 1/1966 | Dreyfus | |
| 3,391,951 A | 7/1968 | Miller | |
| 3,413,097 A | 11/1968 | Jungner | |
| D219,565 S | 12/1970 | Pecker et al. | |
| 3,626,938 A | 12/1971 | Versaci | |
| 3,694,624 A | 9/1972 | Buchta | |
| 3,709,222 A | 1/1973 | De Vries | |
| 3,780,736 A | 12/1973 | Chen | |
| 3,814,680 A | 6/1974 | Wood | |
| 3,840,011 A | 10/1974 | Wright | |
| D234,878 S | 4/1975 | Sikes et al. | |
| 3,916,950 A | 11/1975 | Mongerson et al. | |
| 3,926,556 A | 12/1975 | Boucher et al. | |
| 3,955,922 A | 5/1976 | Moulthrop | |
| 3,957,082 A | 5/1976 | Fuson et al. | |
| 3,986,508 A | 10/1976 | Barrington | |
| 3,994,686 A | 11/1976 | Rauser et al. | |
| 4,055,252 A | 10/1977 | Klamm et al. | |
| 4,056,116 A | 11/1977 | Carter et al. | |
| 4,063,890 A | 12/1977 | Baron | |
| 4,069,153 A | 1/1978 | Gunther | |
| 4,080,965 A | 3/1978 | Phillips | |
| 4,096,859 A | 6/1978 | Agarwal et al. | |
| 4,121,107 A | 10/1978 | Bachmann | |
| 4,141,686 A | 2/1979 | Lewis | |
| 4,169,474 A | 10/1979 | Wagner | |
| 4,173,234 A | 11/1979 | Platt et al. | |
| 4,182,451 A | 1/1980 | Watson | |
| 4,196,730 A | 4/1980 | Wilson | |
| 4,201,917 A | 5/1980 | Graentzel | |
| 4,219,221 A | 6/1980 | Webb | |
| 4,219,055 A | 8/1980 | Wright | |
| 4,239,041 A | 12/1980 | Moncrief et al. | |
| 4,242,310 A | 12/1980 | Greff et al. | |
| 4,291,701 A | 9/1981 | Bowman | |
| 4,306,976 A | 12/1981 | Bazzata | |
| 4,338,933 A | 7/1982 | Bayard et al. | |
| 4,346,703 A | 8/1982 | Dennehey | |
| 4,387,879 A | 6/1983 | Tauschinski | |
| 4,405,315 A * | 9/1983 | Handt ................ | A61M 1/1668 141/330 |
| 4,412,834 A | 11/1983 | Kulin et al. | |
| 4,433,244 A | 2/1984 | Hogan | |
| 4,439,188 A * | 3/1984 | Dennehey ................. | A61J 1/00 138/109 |
| 4,439,193 A | 3/1984 | Larkin | |
| 4,464,336 A | 8/1984 | Hiramoto | |
| 4,475,900 A * | 10/1984 | Popovich .................. | A61L 2/10 604/28 |
| 4,500,788 A | 2/1985 | Kulin et al. | |
| 4,503,333 A | 3/1985 | Kulin et al. | |
| 4,541,829 A | 9/1985 | Munsch et al. | |
| 4,557,727 A | 12/1985 | Handt | |
| 4,596,551 A | 6/1986 | Golinski et al. | |
| 4,617,012 A | 10/1986 | Vaillancour | |
| 4,626,245 A | 12/1986 | Weinstein | |
| 4,626,845 A | 12/1986 | Ley | |
| 4,655,753 A | 4/1987 | Bellotti et al. | |
| 4,655,762 A | 4/1987 | Rogers | |
| 4,675,007 A | 6/1987 | Terry | |
| 4,695,276 A | 9/1987 | Shinno et al. | |
| 4,703,314 A | 10/1987 | Spani | |
| 4,735,240 A | 4/1988 | Ziegler | |
| 4,738,668 A | 4/1988 | Bellotti et al. | |
| 4,744,395 A | 5/1988 | Ziegler | |
| 4,755,292 A | 7/1988 | Merriam | |
| 4,756,706 A | 7/1988 | Kerns et al. | |
| 4,769,017 A | 9/1988 | Fath et al. | |
| 4,774,415 A | 9/1988 | Biegel et al. | |
| 4,779,460 A | 10/1988 | Cruickshank | |
| 4,801,926 A | 1/1989 | Bitetti | |
| 4,804,950 A | 2/1989 | Moon et al. | |
| 4,840,621 A * | 6/1989 | Larkin .................. | A61M 39/18 141/330 |
| 4,869,286 A | 9/1989 | Williams et al. | |
| 4,873,446 A | 10/1989 | Kreitmair et al. | |
| 4,873,623 A | 10/1989 | Lane et al. | |
| 4,878,516 A | 11/1989 | Mathieu | |
| 4,882,496 A | 11/1989 | Bellotti et al. | |
| 4,895,570 A * | 1/1990 | Larkin ............... | A61M 39/1011 604/411 |
| 4,895,657 A | 1/1990 | Polaschegg | |
| 4,898,578 A | 2/1990 | Rubalcaba | |
| 4,914,624 A | 4/1990 | Dunthorn | |
| 4,917,155 A | 4/1990 | Koblasz et al. | |
| 4,925,444 A | 5/1990 | Orkin et al. | |
| 4,942,514 A | 7/1990 | Miyagaki et al. | |
| 4,952,812 A | 8/1990 | Miripol et al. | |
| 4,958,515 A | 9/1990 | Brueggen et al. | |
| 5,014,494 A | 5/1991 | George | |
| 5,047,011 A * | 9/1991 | Caron .................... | A61M 39/18 141/330 |
| 5,056,059 A | 10/1991 | Tivig et al. | |
| 5,057,074 A | 10/1991 | Suzuki et al. | |
| 5,062,774 A * | 11/1991 | Kramer .................... | A61J 3/002 128/DIG. 12 |
| 5,088,515 A | 2/1992 | Kamen | |
| 5,108,063 A | 4/1992 | Koerber et al. | |
| 5,111,184 A | 5/1992 | Heaton et al. | |
| 5,125,911 A | 6/1992 | Grabenkort et al. | |
| 5,178,182 A | 1/1993 | Kamen | |
| 5,184,020 A | 2/1993 | Hearst et al. | |
| 5,187,641 A | 2/1993 | Muskatello et al. | |
| 5,207,642 A | 5/1993 | Orkin et al. | |
| 5,221,267 A | 6/1993 | Folden | |
| 5,230,439 A | 7/1993 | Klok et al. | |
| 5,247,434 A | 9/1993 | Peterson et al. | |
| 5,250,041 A | 10/1993 | Folen et al. | |
| 5,279,605 A | 1/1994 | Karrasch et al. | |
| 5,311,899 A | 5/1994 | Isayama et al. | |
| 5,324,422 A | 6/1994 | Colleran et al. | |
| 5,326,476 A | 7/1994 | Grogan et al. | |
| D349,861 S | 8/1994 | Kanewske et al. | |
| 5,334,139 A | 8/1994 | Jeppsson et al. | |
| D350,823 S | 9/1994 | Lanigan | |
| 5,350,357 A * | 9/1994 | Kamen .................... | A61M 1/28 604/29 |
| 5,399,156 A | 3/1995 | Lindsay | |
| 5,472,614 A | 12/1995 | Rossi | |
| 5,472,720 A | 12/1995 | Rakhimov et al. | |
| 5,482,440 A * | 1/1996 | Dennehey ........... | A61M 1/3693 417/477.2 |
| 5,524,486 A | 6/1996 | Hermann | |
| 5,533,392 A | 7/1996 | Kira | |

(56) References Cited

U.S. PATENT DOCUMENTS

| | | | |
|---|---|---|---|
| 5,540,265 A | 7/1996 | Poiaschegg et al. | |
| 5,540,568 A | 7/1996 | Rosen et al. | |
| 5,542,913 A | 8/1996 | Lindsay | |
| 5,542,919 A | 8/1996 | Simon et al. | |
| 5,572,992 A | 11/1996 | Kankkunen et al. | |
| 5,583,948 A | 12/1996 | Shibayama | |
| 5,591,344 A | 1/1997 | Kenley et al. | |
| 5,609,770 A | 3/1997 | Zimmerman et al. | |
| 5,611,506 A | 3/1997 | Berger et al. | |
| 5,612,001 A | 3/1997 | Matschke | |
| 5,618,441 A | 4/1997 | Rosa et al. | |
| 5,620,608 A | 4/1997 | Rosa et al. | |
| 5,628,908 A * | 5/1997 | Kamen | A61M 1/28 210/180 |
| 5,647,984 A | 7/1997 | Hovland et al. | |
| D383,842 S | 9/1997 | Kenley et al. | |
| 5,674,397 A * | 10/1997 | Pawlak | A61L 2/04 210/436 |
| 5,707,911 A | 1/1998 | Rakhimov et al. | |
| 5,714,119 A | 2/1998 | Kawagoe et al. | |
| 5,733,457 A | 3/1998 | Hovland et al. | |
| D395,085 S | 6/1998 | Kenley et al. | |
| 5,788,851 A | 8/1998 | Kenley et al. | |
| 5,792,419 A | 8/1998 | Williamson et al. | |
| D398,051 S | 9/1998 | Lanigan et al. | |
| 5,800,383 A | 9/1998 | Chandler et al. | |
| 5,807,312 A | 9/1998 | Dzwonkiewicz | |
| 5,843,379 A | 12/1998 | Kristensen | |
| 5,894,089 A | 4/1999 | Ogawa | |
| 5,900,211 A | 5/1999 | Dunn et al. | |
| 5,925,014 A | 7/1999 | Teeple | |
| 5,948,247 A | 9/1999 | Gillerfalk et al. | |
| 5,971,529 A | 10/1999 | Pawlowski et al. | |
| 5,971,972 A | 10/1999 | Rosenbaum | |
| 5,989,423 A * | 11/1999 | Kamen | A61M 1/28 210/180 |
| 6,013,918 A | 1/2000 | Bushnell et al. | |
| 6,106,612 A | 8/2000 | White | |
| 6,121,555 A | 9/2000 | Nowosielski et al. | |
| 6,143,181 A | 11/2000 | Falkvall et al. | |
| 6,146,523 A | 11/2000 | Kenley et al. | |
| 6,146,600 A | 11/2000 | Williamson | |
| 6,171,561 B1 | 1/2001 | Williamson et al. | |
| 6,202,487 B1 | 3/2001 | Urias et al. | |
| 6,219,933 B1 | 4/2001 | Taniguchi et al. | |
| 6,228,332 B1 | 5/2001 | Dunn et al. | |
| 6,234,538 B1 | 5/2001 | Lauer | |
| 6,245,570 B1 | 6/2001 | Grimm | |
| 6,261,065 B1 * | 7/2001 | Nayak | F04B 49/06 417/53 |
| 6,268,997 B1 | 7/2001 | Hong | |
| 6,293,921 B1 * | 9/2001 | Shinmoto | A61M 1/28 604/29 |
| 6,312,074 B1 | 11/2001 | Walker | |
| 6,353,532 B1 | 3/2002 | Landrum et al. | |
| 6,370,951 B1 | 4/2002 | Kerchaert et al. | |
| 6,397,674 B1 | 6/2002 | Kerchaert et al. | |
| 6,440,095 B1 | 8/2002 | Utterberg | |
| 6,443,147 B1 | 9/2002 | Matter | |
| 6,461,568 B1 | 10/2002 | Eckhardt | |
| 6,468,424 B1 | 10/2002 | Donig et al. | |
| 6,472,887 B1 | 10/2002 | Tullis et al. | |
| 6,484,363 B1 | 11/2002 | Herklotz | |
| 6,491,656 B1 * | 12/2002 | Morris | A61M 1/3621 210/257.2 |
| 6,526,824 B2 | 3/2003 | Chase et al. | |
| 6,536,861 B1 | 3/2003 | Usui et al. | |
| 6,565,525 B1 | 5/2003 | Burbank et al. | |
| 6,565,803 B1 | 5/2003 | Bolton et al. | |
| 6,579,253 B1 | 6/2003 | Burbank et al. | |
| 6,595,948 B2 | 7/2003 | Suzuki et al. | |
| 6,622,557 B2 | 9/2003 | Petzold | |
| 6,626,355 B2 | 9/2003 | Sasse et al. | |
| D483,872 S | 12/2003 | Cruz et al. | |
| D484,982 S | 1/2004 | Cruz et al. | |
| 6,696,023 B2 | 2/2004 | Grimm et al. | |
| 6,730,013 B1 | 5/2004 | Shank et al. | |
| 6,736,006 B2 | 5/2004 | Arias | |
| 6,736,797 B1 | 5/2004 | Larsen et al. | |
| D492,034 S | 6/2004 | Cruz et al. | |
| 6,743,201 B1 * | 6/2004 | Donig | A61M 5/44 165/169 |
| 6,752,172 B2 | 6/2004 | Lauer | |
| 6,775,577 B2 | 8/2004 | Cmkovich et al. | |
| 6,799,820 B1 | 10/2004 | Usui et al. | |
| 6,813,868 B2 * | 11/2004 | Baldwin | A61M 5/28 53/411 |
| 6,814,726 B1 | 11/2004 | Lauer | |
| 6,869,158 B2 | 3/2005 | Kojima et al. | |
| 6,911,025 B2 | 6/2005 | Miyahara | |
| 6,913,056 B2 * | 7/2005 | Landherr | A61M 39/146 156/378 |
| 6,923,782 B2 | 8/2005 | O'Mahony et al. | |
| 6,952,963 B2 | 10/2005 | Delnevo | |
| 6,997,905 B2 | 2/2006 | Gillespie et al. | |
| 7,013,727 B2 | 3/2006 | Delnevo | |
| 7,044,927 B2 | 5/2006 | Muelier et al. | |
| 7,055,926 B2 | 6/2006 | Kojima et al. | |
| 7,083,605 B2 | 8/2006 | Miyahara | |
| 7,115,228 B2 * | 10/2006 | Lundtveit | A61M 1/28 422/44 |
| 7,147,613 B2 | 12/2006 | Burbank et al. | |
| 7,157,727 B2 | 1/2007 | Kimura | |
| 7,171,249 B2 | 1/2007 | Takahashi et al. | |
| 7,175,244 B2 | 2/2007 | Usui et al. | |
| 7,188,520 B2 | 3/2007 | Usui et al. | |
| 7,195,615 B2 | 3/2007 | Tan | |
| 7,206,715 B2 | 4/2007 | Vanderveen et al. | |
| 7,232,429 B2 | 6/2007 | Moreci | |
| 7,238,164 B2 * | 7/2007 | Childers | A61M 1/1696 604/6.11 |
| 7,243,893 B2 | 7/2007 | Sohue et al. | |
| 7,267,000 B1 | 9/2007 | Usui et al. | |
| 7,270,386 B2 | 9/2007 | Takahashi et al. | |
| 7,304,583 B2 | 12/2007 | Beller | |
| 7,306,197 B2 | 12/2007 | Parrino et al. | |
| D615,191 S | 5/2010 | McGill et al. | |
| 7,727,220 B2 * | 6/2010 | Wieslander | A61M 39/18 604/403 |
| 7,736,328 B2 * | 6/2010 | Childers | A61M 1/167 604/29 |
| 7,753,085 B2 * | 7/2010 | Tribble | B65B 3/003 141/104 |
| 7,766,301 B2 | 8/2010 | Gray et al. | |
| 7,776,006 B2 | 8/2010 | Childers et al. | |
| 7,905,861 B2 | 3/2011 | Rhinehart et al. | |
| 7,909,795 B2 | 3/2011 | Childers et al. | |
| 7,955,295 B2 * | 6/2011 | Lee | A61M 1/28 604/29 |
| 8,083,709 B2 | 12/2011 | Childers et al. | |
| 8,257,299 B2 | 9/2012 | Childers et al. | |
| 8,361,009 B2 | 1/2013 | Lee et al. | |
| 8,496,609 B2 * | 7/2013 | Childers | A61M 1/14 417/477.2 |
| 8,512,275 B2 | 8/2013 | Childers et al. | |
| 9,242,034 B2 * | 1/2016 | Childers | A61M 1/14 |
| 2003/0022058 A1 | 1/2003 | Chang et al. | |
| 2003/0024880 A1 | 2/2003 | Brandl et al. | |
| 2003/0130606 A1 | 7/2003 | Tuck | |
| 2003/0141009 A1 * | 7/2003 | Landherr | A61M 39/146 156/158 |
| 2003/0220598 A1 | 11/2003 | Busby | |
| 2004/0019313 A1 * | 1/2004 | Childers | A61M 1/1696 604/5.01 |
| 2005/0045548 A1 | 3/2005 | Brugger et al. | |
| 2005/0095153 A1 | 5/2005 | Demers et al. | |
| 2005/0096583 A1 * | 5/2005 | Demers | A61M 5/162 604/15 |
| 2005/0126998 A1 | 6/2005 | Childers | |
| 2005/0209563 A1 | 9/2005 | Hopping et al. | |
| 2005/0277912 A1 | 12/2005 | John | |
| 2006/0211989 A1 | 9/2006 | Rhinehart et al. | |

(56) References Cited

U.S. PATENT DOCUMENTS

| | | | |
|---|---|---|---|
| 2006/0241550 A1 | 10/2006 | Kamen et al. | |
| 2007/0278155 A1* | 12/2007 | Lo | A61M 1/16 210/646 |
| 2008/0015492 A1 | 1/2008 | Biesel | |
| 2008/0015493 A1 | 1/2008 | Childers et al. | |
| 2008/0260929 A1 | 10/2008 | Ursin et al. | |
| 2010/0022967 A1 | 1/2010 | Mendels | |
| 2011/0092894 A1 | 4/2011 | McGill et al. | |
| 2011/0125085 A1 | 5/2011 | McGill et al. | |

FOREIGN PATENT DOCUMENTS

| | | |
|---|---|---|
| DE | 202005016276 | 12/2005 |
| EP | 0311848 | 4/1989 |
| EP | 0482858 | 4/1992 |
| EP | 0575970 | 12/1993 |
| EP | 0687474 | 12/1995 |
| EP | 0 847 769 | 6/1998 |
| EP | 0847769 | 6/1998 |
| EP | 0 956 876 | 11/1999 |
| EP | 1279409 | 1/2003 |
| GB | 2118440 | 11/1983 |
| JP | 7-506518 | 7/1995 |
| JP | 2007-506518 | 7/1995 |
| JP | 08-000725 | 1/1996 |
| JP | 11-319075 | 11/1999 |
| JP | 11-347115 | 12/1999 |
| JP | H11347115 | 12/1999 |
| JP | 2000-033123 | 2/2000 |
| JP | 2000033123 | 2/2000 |
| JP | 2001037874 | 2/2001 |
| JP | 2001-238945 | 9/2001 |
| JP | 2001-513404 | 9/2001 |
| JP | 2002539896 | 11/2002 |
| JP | 2003052813 | 2/2003 |
| JP | 2004-156582 | 3/2004 |
| JP | 2006-034845 | 2/2006 |
| JP | 07-506522 | 3/2007 |
| JP | 2007-509712 | 4/2007 |
| JP | 2008-224315 | 9/2008 |
| WO | WO 88/04181 | 6/1988 |
| WO | 9211046 | 7/1992 |
| WO | WO 94/15099 | 7/1994 |
| WO | WO9420154 | 9/1994 |
| WO | 9625214 | 8/1996 |
| WO | WO9902205 | 1/1999 |
| WO | 99/10028 | 3/1999 |
| WO | WO 99/10028 | 3/1999 |
| WO | 0057935 | 10/2000 |
| WO | 03099355 | 12/2003 |
| WO | WO 2005/042065 | 5/2005 |
| WO | 2005120604 | 12/2005 |

OTHER PUBLICATIONS

Mexican Office Action dated Aug. 16, 2016, corresponding to Mexican Patent Application No. MX/a/2014/011379. 4 pages.

Japanese Office Action dated Dec. 26, 2016, corresponding to Japanese Patent Application No. 2015-114944.

Japanese Office Action dated Oct. 2, 2014 in corresponding Japanese Appln. No. 2013-95010.

Japanese Office Action dated Aug. 7, 2013 in corresponding Japanese Patent Application No. 2010-515249.

Japanese Office Action dated Jan. 30, 2013 in corresponding Japanese Patent Application No. 2010-515249.

European Office Action dated Jan. 3, 2014 in corresponding European Patent Application No. 08 772 342.5.

Mexican Office Action dated Apr. 19, 2013 in corresponding Mexican Patent Application No. MX/a/2010/000291.

Mexican Office Action dated Nov. 22, 2013 in corresponding Mexican Patent Application No. MX/a/2010/000291.

Mexican Office Action—Mexican Appl. No. MX/a/2010/000291—dated Dec. 16, 2014 (3 pages).

European Office Action dated Apr. 2, 2015 in corresponding European Appin. No. 08772342.5 (4 pages).

Japanese Office Action dated Mar. 6, 2014 in corresponding Japanese Appln. No. 2013-95010.

Japanese Office Action dated Feb. 16, 2016, corresponding to Japanese Patent Application No. P2015-075268. 4 pages.

Fresenius Medical Care Sleep-SafeTM Communicating Therapy brochure, copyright 1998.

Fresenius Medical Care Sleep-SafeTM Operating instructions, Part No. 6778051, 1st edition, Oct. 2000.

Fresenius Medical Care Sleep-SafeTM Technical Manual, Part No. 6778071, 1st edition, Aug. 2000.

Fresenius Medical Care Sleep-SafeTM Technical Manual, Part No. 6778071, 2nd edition, Dec. 2001.

* cited by examiner

DIALYSIS SYSTEM HAVING AN AUTOCONNECTION MECHANISM

PRIORITY CLAIM

This application claims priority to and the benefit as a continuation application of and U.S. patent application Ser. No. 13/493,743, filed Jun. 11, 2012, now U.S. Pat. No. 9,242,034, entitled, "Dialysis System Having Autoconnection" and U.S. patent application Ser. No. 11/773,522, filed Jul. 5, 2007, now U.S. Pat. No. 8,496,609, entitled, "Fluid Delivery System With Spiked Cassette", the entire contents of each of which are incorporated herein by reference and relied upon.

BACKGROUND

In general, the present disclosure relates to medical fluid delivery systems that employ a disposable cassette. In particular, the present disclosure provides systems and methods for cassette-based dialysis medical fluid therapies, including but not limited to those using peristaltic pumps and diaphragm pumps.

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue. Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. Hemodialysis treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Peritoneal dialysis uses a dialysis solution, or "dialysate," which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment. Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

Hemodialysis, APD (including tidal flow) and CFPD systems can employ a pumping cassette. The pumping cassette typically includes a flexible membrane that is moved mechanically to push and pull dialysis fluid out of and into, respectively, the cassette. Certain known systems include flexible sheeting on one side of the cassette, while others include sheeting on both sides of the cassette. Positive and/or negative pressure can be used to operate the pumping cassettes. Cassettes with other pumps or fluid transfer mechanisms may be used.

There are two concerns for patient using dialysis treatments, especially for home-use peritoneal dialysis. Dialysis patients tend to be elderly, with many aged 50 or 60 years, and older. Connecting bags of dialysis fluid to a treatment machine may be difficult because of the force required to push a connecting spike through a sealing membrane. This force can be as much as 20 lbs or more, and may be required to connect each of four bags every night. The force and physical dexterity required make it difficult for significant numbers of patients to make the connections properly, e.g., without spiking through a connecting line, rather than a sealing membrane. The difficulty encountered in making connections may lead to improper touching and contamination of one or more of the lines, if the patient inadvertently grasps or touches a connector or an portion which is sterile and is intended to remain sterile. Inadvertent touches can lead to infections and peritonitis, and may require hospitalization or other stressful procedures.

Accordingly, what is needed is a better way to connect containers of dialysis solutions to a dialysis machine, such as a peritoneal dialysis machine. The present disclosure addresses the above-described needs and concerns.

SUMMARY

A first embodiment is a dialysis cassette. The dialysis cassette includes a frame, at least one pump chamber within the frame, first and second flexible membranes joined to opposite sides of the frame, a plurality of valves for routing liquid within the cassette, and a plurality of ports communicating with the valves, each port including an integral spike, the ports configured for connection with sources of dialysis fluid.

Another embodiment is a dialysis cassette. The dialysis cassette includes a frame, at least one pump chamber within the frame, first and second flexible membranes joined to opposite sides of the frame, a plurality of valves for routing liquid within the cassette, and a plurality of ports in a row and communicating with the valves, each port including an integral spike, the ports configured for connection with a source of dialysis fluid, the spikes protruding in sequentially greater distances from the cassette, the distances from about ⅛ inch to about ½ inch.

Another embodiment is a dialysis cassette. The cassette includes a rigid frame, at least one pump chamber within the frame, a plurality of valves for routing liquid within the cassette, a plurality of ports arranged communicating with the valves, the ports configured for connection to tubing, and first and second flexible membranes joined to opposite sides of the frame, wherein the membranes are configured to cover the at least one pump chamber and the valves and not to cover the ports.

Another embodiment is a dialysis cassette. The dialysis cassette includes a rigid frame, at least one pump chamber within the frame, a plurality of valves for routing liquid within the cassette, a plurality of ports communicating with the valves, the ports perpendicular to a longitudinal axis of the frame, the ports also configured for connection to tubing, and first and second flexible membranes joined to opposite sides of the frame, wherein the membranes are configured to cover the at least one pump chamber and the valves and not to cover the ports.

Another embodiment is a method for connecting fluid containers. The method includes steps of placing a connector from a fluid container into an autoconnect machine, placing a tubing cap from tubing from one of the fluid containers into a pocket of one of a plurality of fingers of the autoconnect machine, causing the finger to move or rotate in a direction toward a dispensing cassette on a different side of the fingers, and translating the tubing and the tubing cap a distance in a direction toward the cassette, wherein translating rotates the plurality of fingers and causes only the finger into which the tubing cap was placed to capture a port cap from a port of the cassette, the cassette including at least one pump chamber and a plurality of ports in a row and a plurality of port caps, each port including an integral internal spike, wherein the spikes protrude from the cassette different distances, the distances differing by about ⅛ inch to about ½ inch. The method also includes steps of translating the tubing in a direction away from the cassette, removing the tubing cap from the tubing and leaving the tubing cap from the tubing in the pocket, rotating the fingers away from the cassette and in a direction to remove the port cap from the port of the cassette, and translating the tubing toward the cassette and causing a spike in the port of the cassette to pierce a sealing membrane in the tubing, wherein the method is suitable for fluid containers for peritoneal dialysis or hemodialysis.

As will be clear from the disclosure below, an autoconnect device may be used for both peritoneal dialysis and hemodialysis. In addition, embodiments of an autoconnect device may be used for dispensation or administration of other fluids with devices other than dialysis or hemodialysis machines, such as for blood or blood-substitute transfusions. Additional features and advantages of the present disclosure are described in, and will be apparent from, the following Detailed Description of the Disclosure and the figures.

DETAILED DESCRIPTION

Figure 1:
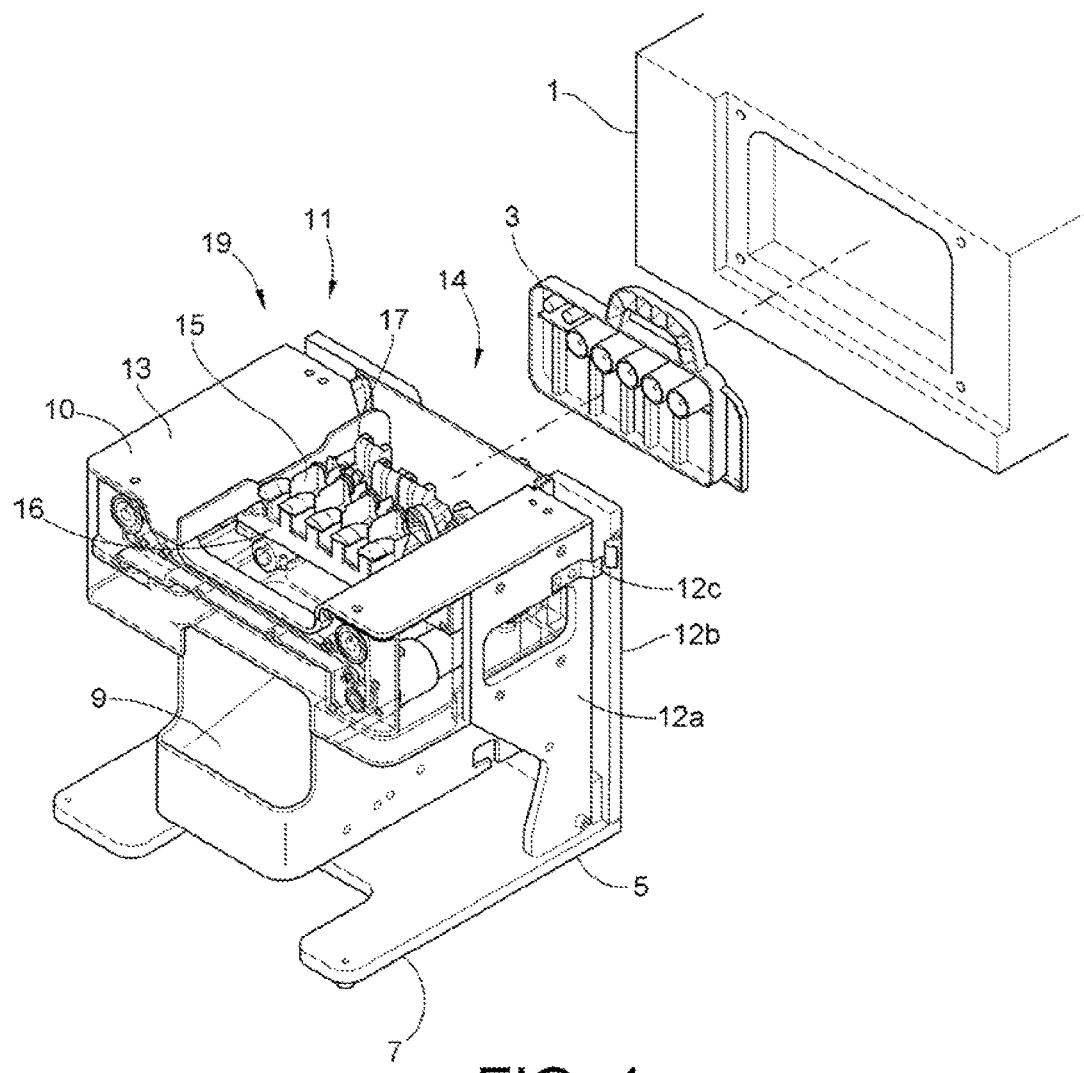
FIG. 1 is an exploded view of a first embodiment of an autoconnect mechanism used with a disposable cassette and a dialysis machine.

The present disclosure relates to medical fluid delivery systems that employ a pump, such as a diaphragm pump or a peristaltic pump. In particular, the present disclosure provides systems, methods and apparatuses for cassette-based dialysis therapies including but not limited to hemodialysis, hemofiltration, hemodiafiltration, any type of continuous renal replacement therapy ("CRRT"), congestive heart failure treatment, CAPD, APD (including tidal modalities) and CFPD. The cassette is disposable and typically discarded after a single use or therapy, reducing risks associated with contamination. The autoconnect device is intended for reuse as a part of the dialysis machine.

Patient Care

An autoconnect device, as discussed below, is intended to ease the burden on dialysis patients, who may be elderly and in poor health, and those who care for them, who may also be elderly, and who may also be in poor health. The daily task of hooking up dialysis fluid bags is indeed difficult for those with limited strength. In addition, it is easy to inadvertently break sterility or to contaminate the instrument or the container of fluid. In general terms, and for which a detailed explanation is given below, the autoconnect device works in the following manner.

After the cassette is loaded into the dialysis machine, the user attaches tubing from one or more dialysis bags by laying tubing in the top portion of the device and by placing caps from the tubing in the tops of special fingers on the top of the device. The autoconnect machine is then activated. A series of pinchers or occluders grasps the tubing and a shuttle then moves the tubing forward with the shuttle. The forward movement also causes the fingers to rotate forward, in the direction of the shuttle motion and toward the dialysis disposable cassette. Only those fingers with a tubing cap will rotate sufficiently to contact a shielding cap from a port of the dialysis disposable cassette. These fingers are rotated into the shielding cap or caps and grasp the cap or caps. After this forward rotation, the shuttle reverses direction, and the cap from the tubing, held in place by a restraining orifice atop the finger, is removed by remaining stationary while the shuttle and the tubing moves backward. The finger is now rotated in the opposite direction, while grasping the cap from the disposable cassette port, the rotation causing the cassette port cap to remain in the top of the rotating finger, thus removing the port cap. Both caps have now been removed without the user touching the caps.

The top of the finger (or fingers) now contains a cap from the tubing and a cap from the cassette port. The fingers are then rotated downward, causing the caps to fall from the tops of the fingers into a chute, drawer, or other area. The fingers remain in the downward position while therapy is in progress. Once the caps are disposed of, the shuttle again reverses direction. At this point, the caps have been removed and all that remains before dialysis is to connect the end of the tubing, with its sterile seal, to the cassette port, which is also sterile. The shuttle now translates forward pushing on the connector while the tubing is held in place by the occluder, and extends the tubing into a piercing needle contained within the cassette port. The piercing needle is preferably somewhat recessed from the outer lip of the port for ease of maintaining the sterile environment and a sterile connection. Once the needle pierces the membrane seal of the dialysis tubing, the connection is made and will remain secure. With the dialysis containers now attached via a sterile connection, an after the occluder is released, dialysis may now begin. In the embodiments discussed below, the autoconnect device may be used to connect from one to five containers of dialysis fluid. Other embodiments may be used to connect less than five or more than five containers. Still other embodiments may be used for one or more fluid containers other than dialysis fluid, such as blood, blood substitutes, saline solution, nutritional fluids, medications, and others. For example, one of the containers may include a neutral fluid, such as saline, and a medication needed by the patient, such as heparin, insulin, or an antibiotic. These medication fluids may just as easily be used with the autoconnect device and a device for downstream infusion or dispensing.

The Autoconnect Device

Referring now to the drawings and in particular to FIG. 1, a dialysis machine 1 is intended for use with a disposable dialysis cassette 3 and an autoconnect machine 5. Autoconnect machine 5 in this embodiment includes a frame or base 7, a central area 9 for disposal of caps from the dialysis cassette and from bags of dialysis fluid. In this embodiment, frame 7 includes sides 12a and back portions 12b, joined by hinges 12c. Main chassis 10 includes a central area 11 includes discrete portions of channels 14 for tubing from the dialysis bags. Autoconnect 5 also includes top covers 13 on either side to shield and protect the inner workings. Also included in top working area 19 is a shuttle 15 for advancing the tubing, an occluder 16, and fingers 17 for removing caps from the dialysate bags and from the dialysis cassette.

In using the autoconnect device, a plurality of containers of dialysis fluid may be positioned in the vicinity of the dialysis machine or near the autoconnect device. Since dialysis bags typically include tubing about 2 feet long, either position is possible and may be suitable. If the dialysis machine includes one or more facilities for heating, the containers of dialysis fluid are desirable heated to a temperature close to body temperature before use. Alternatively, the disposable dialysis cassette may include provisions for heating dialysis fluid as it is being pumped. For example, the dialysis cassette 30 depicted in FIG. 3A may be used to warm the dialysis fluid.

Figure 2:
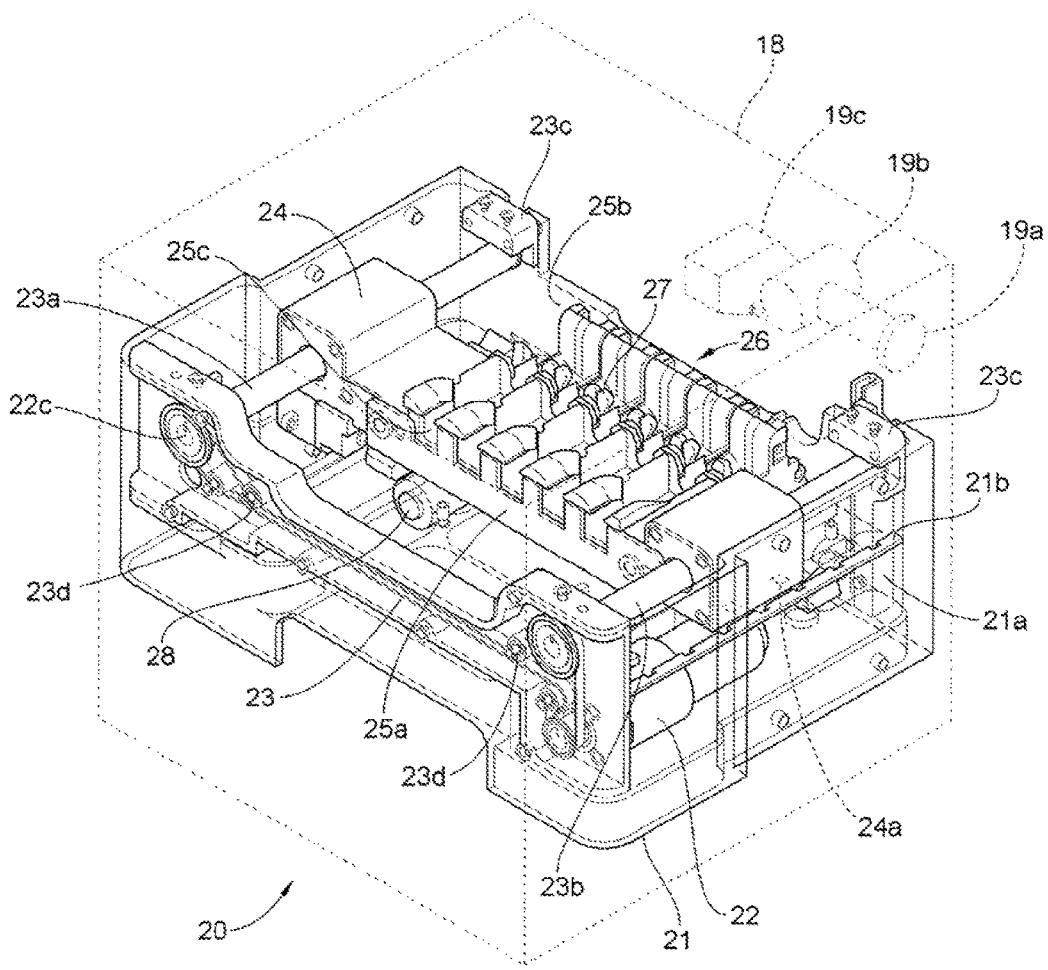
FIG. 2 is an isometric view of a second embodiment of an autoconnect mechanism for use with a dispensing machine.

The embodiment of FIG. 1 may be used as presented for automatically connecting containers of dialysis fluid to the pumping cassette while preserving a sterile connection. Alternatively, the main chassis portion may be used separately, as shown in FIG. 2, as an autoconnect device 20. Autoconnect 20 includes a frame 21, frame back wall 21a, and also includes a drive motor 22 and a drive system 23 for positioning shuttle 24. Drive system 23 includes left and right lead screws 23a, 23b, and a power transmission system as shown, including a timing belt, and belt tensioners as needed, to distribute power from motor 22 to the two lead screws. The system could use gears rather than a timing belt. Drive system 23 includes at least mounts 23c and bearings 23d as shown, and also preferably includes a drive train and any necessary gear reduction for matching motor 22 to the desired speed for advancing and retracting shuttle 24. A brushed 24 VDC planetary gear motor, with a suitable controller, has been found satisfactory for the motor for this application. Other suitable motors may be used.

Autoconnect 20 includes a central area 26 with discrete channels for tubing from dialysis containers, and also includes front occluder 25a and a rear occluder 25b for occluding or pinching tubing from the dialysis containers. In this embodiment, central area 26 includes five channels for placement of tubing from five dialysis containers. Occluders 25a, 25b each include openings for the tubing, in this case five openings 25c. In one embodiment, occluders 25a, 25b are both part of a single, U-shaped piece of sheet metal, in which occluder 25a performs the occlusion function, i.e., pinching the tubing so no flow is possible, while occluder 25b acts only to secure the membrane port into shuttle 24. When the occluder is actuated and no flow is possible in the tubing, there will be no premature flow of fluid during spiking, and the machine may, with confidence, perform an integrity test. There are also five fingers 27 for grasping and removing caps from the ends of the dialysis tubing, and also for grasping and removing caps from the ports of a dialysis cassette used with the autoconnect and a dialysis machine. Visible also in FIG. 2 is a motor 28 for rotating fingers 27. A brushed 24 VDC planetary gear motor, with a suitable controller, has also been found satisfactory for this application. Other suitable motors may be used.

Autoconnect device 20 preferably is enclosed in a housing 18, to protect the device. The housing preferably also includes ducting 19a connected to a blower 19b and HEPA or other filter 19c. The filter provides clean air to the blower which can keep the housing under a slight positive pressure during use, thus preventing dust, mold, and the like from entering the atmosphere of the device. This embodiment of an autoconnect device works in the following manner. A user furnishes one or more containers of dialysis fluid and tubing for the containers, the tubing including a special cap for connecting via the autoconnect device. The tubing connects to the containers and the tubing is then connected to the dialysis machine via a disposable cassette. The special cap is placed into the near side of the rotating finger and the tubing is laid into the channel atop the autoconnect device. The autoconnect device then begins its automatic sequence for connecting one or more containers of dialysis fluid to the dialysis machine.

The occluder translates to the left, thus grasping the tubing and holding it immobile within the shuttle. The shuttle translates forward, and each finger with a cap causes that finger to rotate forward, in the direction of the shuttle movement. The movement of the finger causes the finger to grasp the cap from a port on the disposable cassette. The shuttle is now translated backward, away from the disposable. The finger, with the tubing cap atop, is captured by the port cap. When the shuttle translates backward, the tubing cap is removed because it is restrained within the finger. After the shuttle translates backward, the fingers rotate in a backward direction. Since the cap or caps from the disposable ports are captured by one or more fingers, this rotation removes the cap or caps. Further rotation below horizontal causes the caps to fall from the finger or fingers into a bin or open area below the fingers.

Movement of the shuttle, the occluder, and the fingers is controlled by a controller or microcontroller of the autoconnect device. As part of the controls, the shuttle is equipped with an optical sensor 24a, mounted on the bottom portion of the shuttle. The optical sensor 24a is guided by a stationary sensor track 21b, mounted in parallel with the lead screws. Sensor track 21b includes a series of notches as shown. The notches allow the optical sensor to keep the controller informed of the position of the shuttle. As will be obvious to those with skill in the art, other sensors or techniques may be used, such as an encoder on shuttle motor 22, a proximity sensor mounted on the shuttle and targets placed at appropriate locations along the shuttle path, and so forth. For example, a hall effect sensor mounted on the shuttle may be used to detect its position by placement of magnets or other targets along the shuttle path. Alternatively, a position sensor for detecting a position of the shuttle may be placed on the frame with notches, magnets, or the like placed on the shuttle.

Spiked Disposable Cassettes

The autoconnect device is not limited to the embodiments above. For instance, other dialysis disposable cassettes may include the spiked model depicted in FIG. 3A. Disposable cassette 30 includes a housing 31, front and rear flexible membranes 30b, 30c, four ports 30d for sensors, such as conductivity, pH or temperature sensors, heating tube 32 and five ports 33 in a row for connecting to dialysis fluid connectors. Membranes 30b, 30c do not cover the ports 33, 35a, 35b, so that an autoconnect machine, described below, can more easily make the tubing connections to the ports. The ports are perpendicular to a longitudinal axis AA of frame or housing 31 and are also perpendicular to the entire cassette 30.

Each port includes a cap 34 with a protruding, stepped central portion 34a. This protruding portion makes it easier for the autoconnect rotating fingers (discussed below) to grasp the cap. In one embodiment, port 35a is used for the drain line, and port 35b is used for the patient input/output lines. This particular model of a disposable cassette may require an autoconnect device in which the tubing on the shuttle is oriented in a vertical direction, rather than in a horizontal direction. The shuttle will still translate back and forth toward and away from the cassette, and the occluders will translate in a direction perpendicular to the movement of the shuttle. The fingers will be oriented for rotation in a horizontal plane, rather than vertical. When the caps are removed, they will fall away from and to the right of the autoconnect device. The ports have spikes, visible in FIG. 3B below.

Figure 3A:
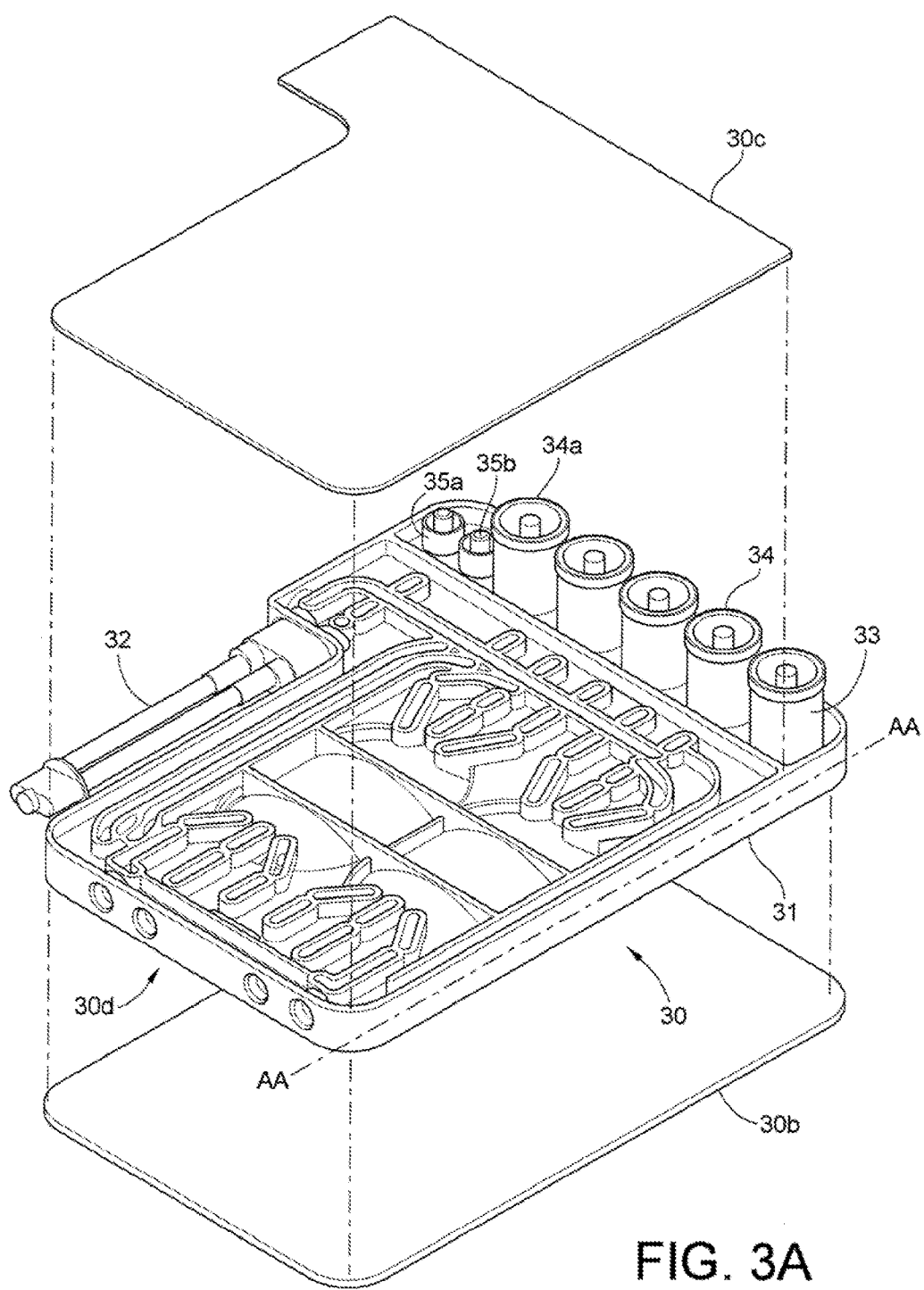
FIGS. 3A and 3B are isometric views of alternate embodiments of disposable cassettes for use with an autoconnect mechanism and a dialysis machine.

In another embodiment of a cassette, not shown but very similar to cassette 30 in FIG. 3A, the ports of the cassette are used differently, and the external connections are also connected differently. First port 35a, on the left, is used to return dialysate from the patient, second port 35b is used to pump dialysate to the patient, and the third port, corresponding to cap 34, is used as the drain. Tubing is connected appropriately. This arrangement may be used for regular dialysis, or may also be used for low-recirculation or pediatric dialysis. For example, pediatric patients may use much smaller volumes of dialysate, with much smaller volumes for recirculation. With very small babies, volume could be as low as 50 ml, while the spent dialysate in the tubing to/from the patient and the cassette could be as much as 15 ml. Separate lines to and from the patient avoid reuse of spent dialysate to the maximum extent possible. This embodiment also has the advantage that ports 35a, 35b, to and from the patient, can be occluded easily and simultaneously, since they are adjacent. This feature could be very useful in the event of a power failure or system malfunction. Other embodiments may use the ports for other functions, with the internal plumbing of the cassette arranged in an appropriate manner.

The port caps 34 have symmetry, preferably radial symmetry. The caps are also preferably radiation-sterilizable and steam-permeable, and are made from low density polyethylene (LDPE). LDPE is able to form a tight seal against the cassette port, protecting the sterility of the port. Other relatively soft materials may be used, but the stepped tips or nipples should be able insert themselves within the jaws of the rotating fingers. Other embodiments may use non-stepped nipples or central portions. The wider next portion of the nipple causes a slight interference with the jaws, and allows the caps to be pulled off the ports when the fingers rotate downward. Besides LDPE, other materials may be used, such as PVC, (poly-vinyl chloride), polyisoprene, silicone and other suitable sterilizable materials.

The disposable cassettes as depicted in FIGS. 1 and 3A-3D have ports that are perpendicular to the normal direction of the ports, which are typically oriented in a direction parallel to a longitudinal axis AA of the cassette. Cassettes with perpendicular ports are easier to manufacture, since the ports and their shrouded spikes may be made with a more complicated injection molding tool, but with no added mold parts, such as cross-slides, and the like. Of course, cassettes with spikes may also be molded with the ports and spikes parallel to the cassette longitudinal axis. These cassettes may be used for both peritoneal dialysis and for hemodialysis.

Figure 3B:
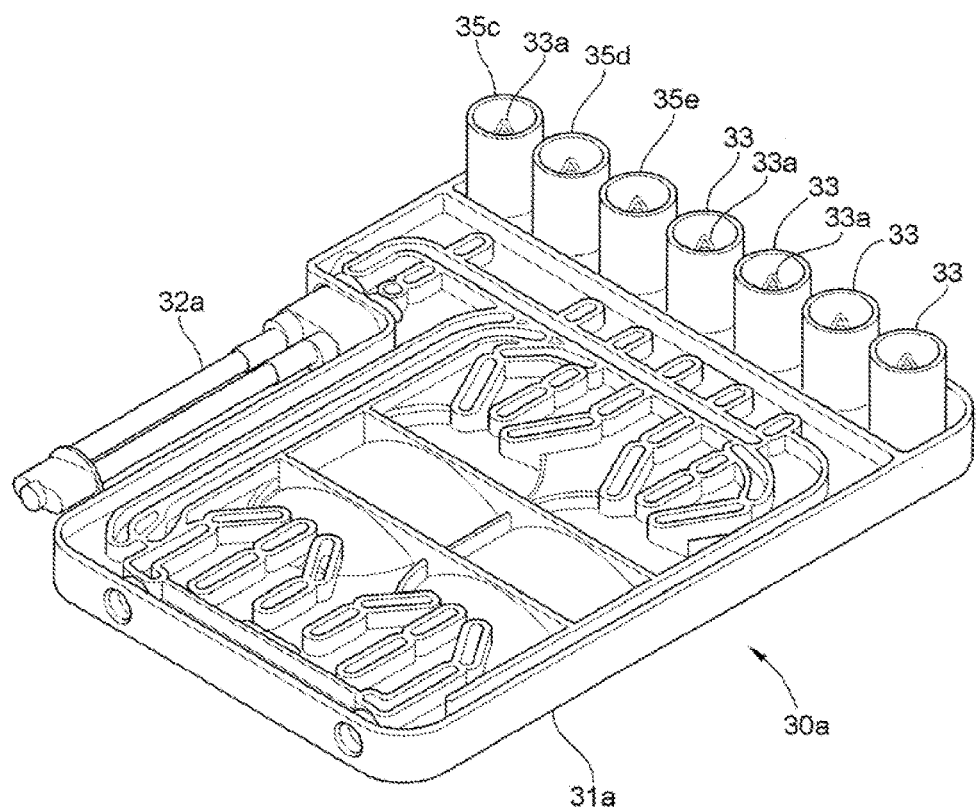

FIG. 3B is an alternate embodiment of a cassette suitable for use with an autoconnect device. Cassette 30a is similar to cassette 30, in that it includes a front portion 31a (shown), a back portion (not shown), a heating tube 32a, and four ports 33 in a row with spikes 33a for containers. In addition, port 35c is provided for connection to the patient, and port 35d for the drain, and port 35e is used return from the patient. The other ports also have spikes 33a for making tubing connections. Rather than using the same port and line for to and from the patient, separate lines are used to help preserve the purity of the dialysate or other fluid, especially for pediatric patients, as noted above. Of course, for hemodialysis, the ports "to and from the patient" are used for "to and from the dialyzer."

Figure 3C:
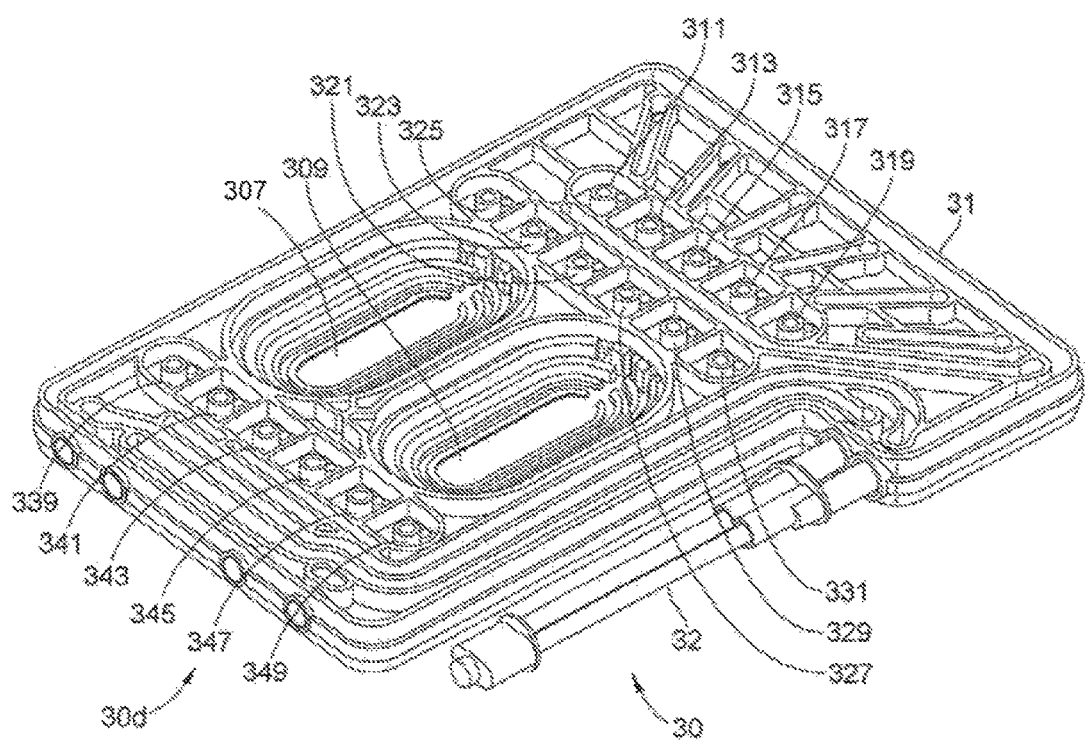
FIGS. 3C and 3D are additional views of cassettes with integral spikes.
Figure 3D:
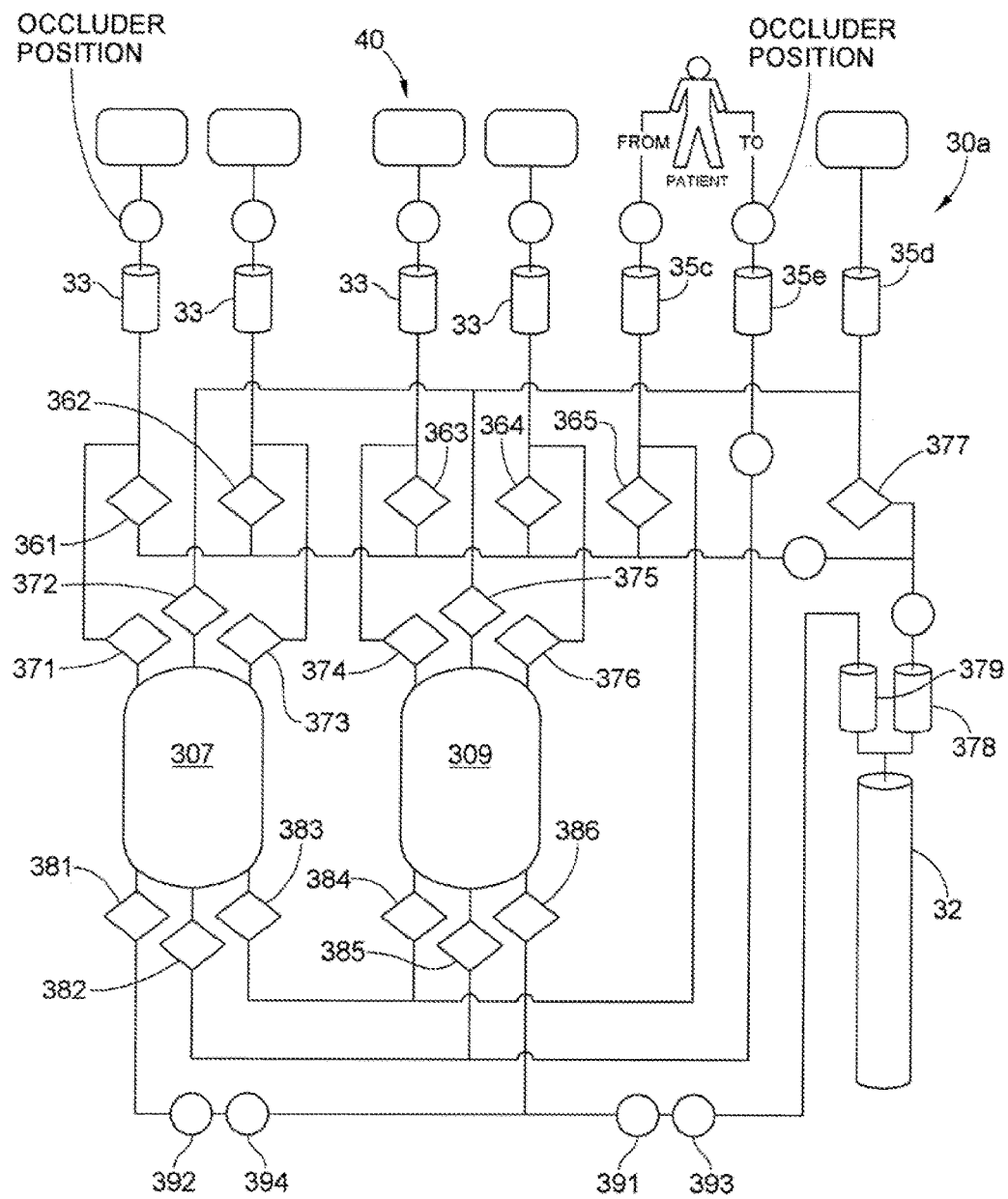

The back side of a spiked cassette 30 is depicted in FIG. 3C, while a schematic of the spiked cassette 30a is depicted in FIG. 3D. The back side of spiked cassette 30 shows details of the flow paths and features of the cassette. Frame 301 is preferably made of a rigid plastic, resistant to deformation, while the flexible membranes 30b, 30c are made from a resilient material, such as a flexible plastic or an elastomer. Examples of the more rigid material include PE, PP, PVC, polysulfone, polycarbonate, acrylic, cyclo-olefin copolymers (COCs), and the like. Examples of materials for the membranes include sterile and inert plastic or rubber. For example, the membranes can be made of nitrile, butyl, Hypalon, kel-F, kynar, neoprene, nylon, polyethylene, polystyrene, polypropylene, polyvinyl chloride, silicone, vinyl, Viton or any combination of these The rigid material enables the flow paths and valves to hold their shape during repeated uses and cycles of operation. In this embodiment, the ports 33, 35c, 35d, 35e are also not covered by membranes 30b, 30c, but the ports are visible and easily available for connection.

The back side of the cassette, depicted in FIG. 3C, includes valves 311, 313, 315 317, and 319 connecting the sources 33 and containers 40 to the heater. Valves 321, 325, 327, and 331 connect, respectively, the left and right pump chambers 307, 309 to the sources of dialysate fluid, while valves 323 and 329 connect the left and right pumps to drain 35b. Other embodiments may have only one pump chamber or more than two pumping chambers. Valves 339, 349 connect the pumps to the heater, while valves 341, 347 control the flow of fluid from the pumps to the patient. Valves 343, 345 connect lines from the patient to the pumps. FIG. 3D includes a more graphic depiction of the valves for cassette 30a. The sources 33 of dialysate or other fluid connect to heater 32 through valves 361, 362, 363, 364. Valves 371, 373 connect left pump 307 directly to sources 33, while valves 374, 376 connect right pump 309 to sources 33. Of course, in most instances, the fluid is desirably warmed, and the flow of fluid to the heater is controlled through port 378 to the heater and port 379 from the heater to the left and right pumps 307, 309, through valves 381, 386. The fluid is then pumped to the patient through valves 382, 385 and port 35e. Fluid is returned from the patient through port 35c, valves 383, 384, and to drains 35d through valves 372, 375. Alternatively, fluid returned from the patient may be routed through valve 365 to the heater. Valve 377 is opened when fluid is to be routed from the heater to drain 35d. Valves 372, 375 are opened to route fluid from the pumps to drain 35d. Of course, other embodiments are possible and are contemplated.

Fluid Containers

Figure 4A:
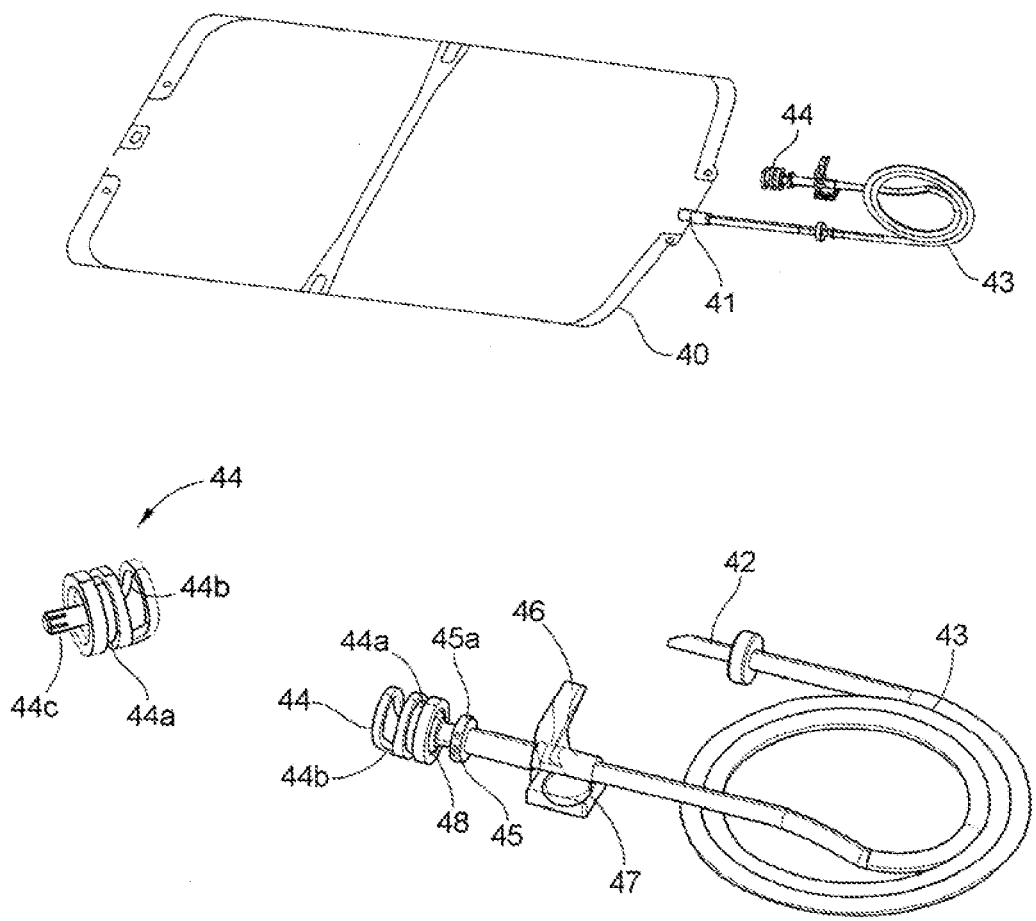
FIG. 4A is an exploded view of a container of dialysis fluid, tubing for use with the container, and a cap for maintaining a sterile end of the tubing.

A closer view of a typical dialysis fluid container is depicted in the exploded view of FIG. 4A. Dialysis bag 40 includes an outlet connection 41 and is used with tubing 43 and a tubing connector 42 for connecting to dialysis bag 40. Tubing 43 includes a housing 46 for a radio-frequency identification (RFID) tag 47. RFID tag 47 is used to identify this particular container and lot of dialysis fluid when the tubing is placed into the autoconnect device and the tag is read. The tubing also includes a flanged handle 45 and a membrane port 45a (internal to the tubing) or internal seal. Tubing 43 is terminated with a cap 44, the cap including a groove 44a, a fold-down handle 44b, and a core pin 44c. Groove 44a is preferably about 2.5 mm wide and about 2.0 mm deep. The handle is useful for removing the cap manually if an autoconnect device is not available. The core pin 44c is used for interfacing and with the internal portions of tubing 43, to preserve the dimensional stability of the tubing up to internal membrane 45a.

The tubing 43 and membrane port 45a may be made from PVC, and the tube cap 44 is preferably a relatively soft material, both the tubing and the tube cap steam are preferably steam sterilizable and steam permeable materials. Very soft silicone, with a Shore A durometer reading of about 35 is preferred, although other materials, with a durometer from 50-100 may also be used. Polyisoprene may be used, as may many styrenic block copolymers, such as those produced by Kraton Polymers, LLC, Houston, Tex., USA. Any of the softer, steam permeable grades will work well in the application. In one embodiment, tube cap 44 may also serve as the RFID housing.

RFID housing 46 is easier to handle and install in the translating shuttle if the housing is a little stiffer. For example, the housings may be made of HDPE, polycarbonate, harder PVC, or other material with a higher Young's modulus. If housing 46 is more rigid, it is easier to insert into the channels of the autoconnect shuttle. The RFID housing need not take the shape disclosed herein, which is configured for ease of placement onto the shuttle. The housing may be any convenient and useful shape that will reliably adhere to the tubing or even to the bag of fluid. In some embodiments, the RFID chip is placed into the housing in a secure manner, such as with a snap-fit. In other embodiments, the RFID chip is insert or over-molded into the housing. In the embodiments disclosed below, the RFID housing is configured for placement over the tubing, for ease of installation onto the shuttle. In other embodiments, the RFID housing may be placed or adhered onto the bag or container of fluid, and is read by a single RFID reader on board the frame or the shuttle. The autoconnect system then directs the user to connect the tubing to a particular channel on the shuttle. Thus, the controller knows the location of each connector and how to utilize each container.

Figure 4B:
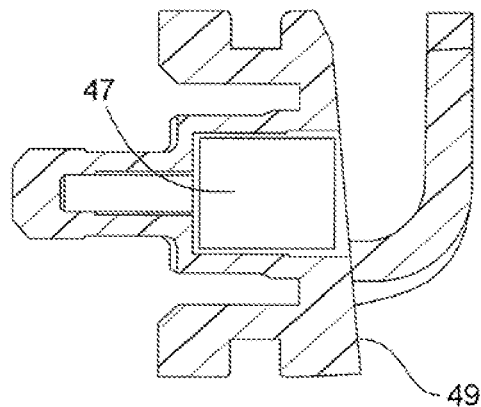
FIGS. 4B and 4C are alternate embodiments of a cap with an RFID chip or other direct part marking feature.
Figure 4C:
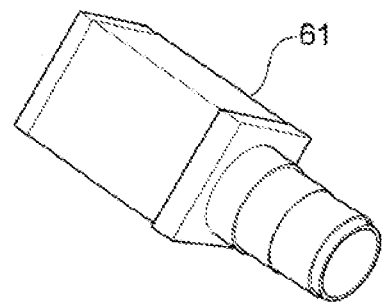
Figure 4C:
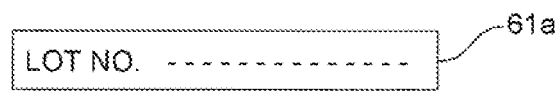
Figure 4C:
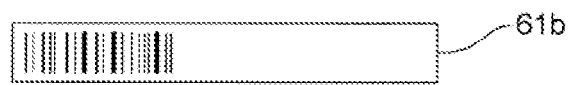
Figure 4C:

In some embodiments, as shown in FIG. 4B, the RFID chip may be assembled or otherwise installed into the cap itself, without a separate housing for the RFID chip. Using this technique, each rotating finger 27, as shown in FIG. 2, will include an RFID reader, to read the chip and report back to the autoconnect controller. Thus, tubing cap 49 will include RFID chip 47 and will be read by an IR reader in the finger 27 in which the cap is placed. In other embodiments, the cap of the tubing, or even the tubing itself, may include a mark as shown in FIG. 4C. In versions using direct parts marking, appropriate information about the solution to be administered, such as the solution, the lot number, and so forth, may be marked onto the cap or the tubing directly. Marks may be made by imprinting, for example, by stamping or ink-jet or other printing method, as shown by imprinted mark 61a. Marks may also be made by placing a bar code indicia, 61b, or by etching a mark 61c. Etching may be accomplished by laser marking, for example. The marked cap or tubing may be detected by a camera 61 mounted on the autoconnect frame and operably connected to the autoconnect controller or the dialysis machine controller.

Placement and Identification of Tubing and Operation of the Occluders

Figure 5A:
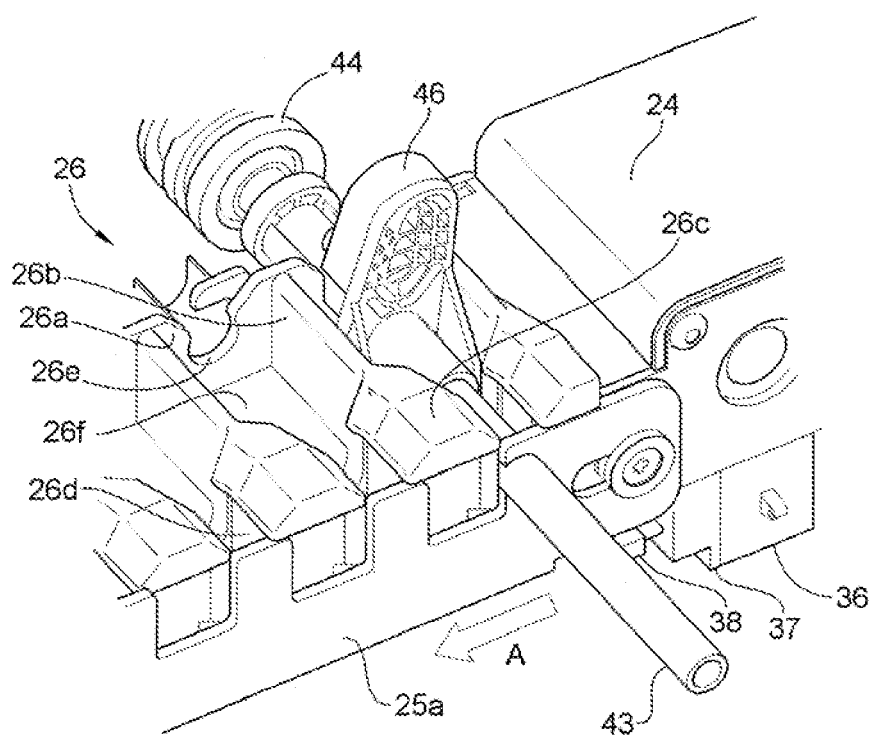
FIGS. 5A, 5B and 6 depict the occluder and the occluding mechanism.
Figure 5B:
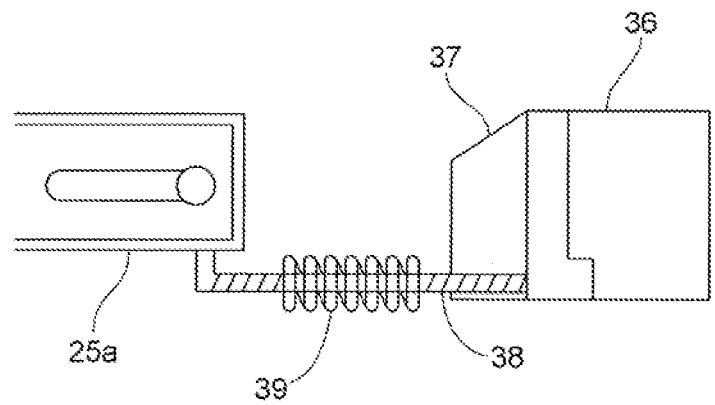
Figure 6:
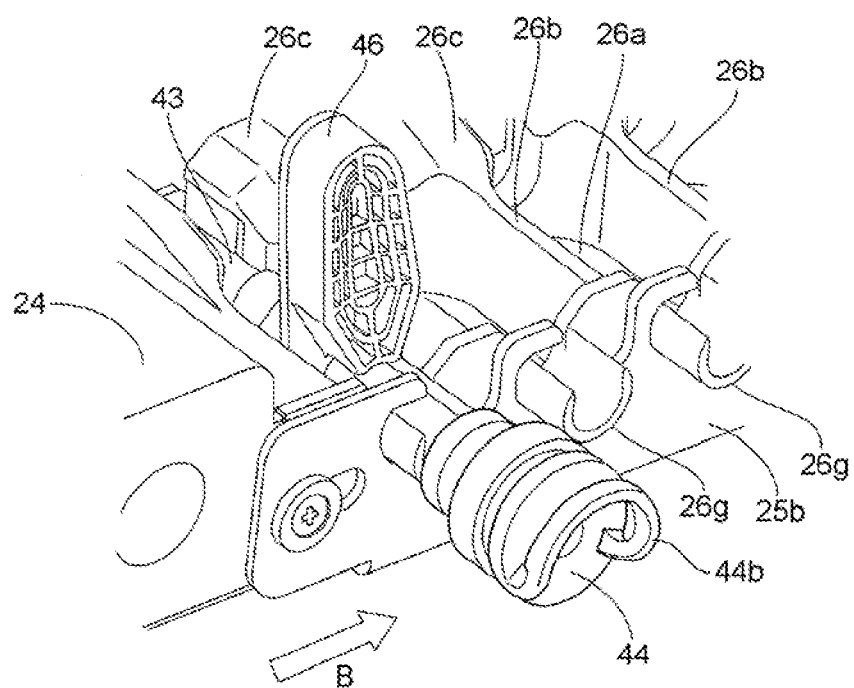

The placement of tubing from the dialysis containers, or tubing from other containers, is depicted in FIGS. 5A, 5B and 6. FIG. 5A depicts a view of shuttle 24 from the tubing side, while FIG. 6 depicts the view from the opposite or disposable side. FIG. 5B shows a close-up of the occluder drive mechanism. Autoconnect device central area 26 includes one or more channels 26a for tubing. Each channel 26a includes side walls 26b with shroud 26c, back end wall 26d, front end wall 26e, and an RFID reader 26f. End walls 26d, 26e include rounded orifices to accommodate the tubing. In one embodiment, the channels 26a and the RFID housing 46 are designed so that the RFID housing is retained in a releasable snap fit once it is inserted into the channel. The RFID reader is intended to read the RFID tag 47 placed in each RFID housing 46 as discussed above.

Occluder 25a has been translated to the left in the direction of arrow A, capturing tubing 43 between occluder 25a and shroud 26c. Occluder 25a is translated using a 6 VDC gear motor 36 mounted on the shuttle, with a suitable speed reduction gearbox 37 and a lead screw 38 mounted to the occluder. Both occluders move at the same time. In some embodiments, spring 39 may used to bias the occluder to a closed position. In other embodiments, the spring may be placed, for instance on the opposite end of the occluder, to bias the occluder open. In yet other embodiments, the control circuitry may include a large capacitor to assure sufficient energy to drive the occluder to a safe closed position as a fail-safe mechanism. At this point, the seals upstream of the tubing may not have been broken, and there may be no fluid in the tubing. The purpose of the occluder, or grasping mechanisms, is to occlude the tubing lumen and also to grasp the tubing to advance the tubing or, as will be seen, to retract the tubing and automatically remove the tubing cap. It will be understood that a solenoid or an air cylinder, or other mechanism, may be used to slide the occluder back and forth on its mounts or mounting pins rather than a lead screw.

Some embodiments may not use occluders. As discussed below, the tubing from the container fits tightly into a housing for an RFID chip. With only a small amount of friction, the tubing will adhere to the RFID housing and will follow along when the RFID housing is placed onto the shuttle. The tubing will also remain in place in the housing when the shuttle is advanced a short distance back and forth within the frame to remove the tubing cap and to pierce the tubing membrane. Some embodiments may thus not use occluders, but the tubing will still travel with the shuttle, moving when the shuttle moves under the influence of normal friction between the housing and the tubing. It any event, the occluder may be useful for other reasons, such as preventing loss of fluid during spiking, or allowing the controller to conduct connection integrity tests. Failsafe closure, described above, may help prevent cross-contamination in case of a power failure.

RFID chip housing 46 is sized to fit within channel 26a, possibly with a snap fit. As seen from FIG. 6, from the opposite side of shuttle 24, back occluder 25b has been translated to the right, in the direction of arrow B to capture tubing 43. While arrows A and B seem opposite, the directions are the same because FIG. 5A views the shuttle from the tubing side, while FIG. 6 views the shuttle from the disposable cassette side. Each channel 26a includes a front collar 26g extending toward the cassette. In addition to the collapsible handle 44b on the tubing end 44, RFID housing 46 may also serve as a handle for placing tubing in the channel. The RFID chip should be durable and rugged, and should be able to withstand sterilization, whether by gamma-ray irradiation, steam autoclaving, typically conducted at about 1 atm gage pressure at 121° C., or by chemical methods.

RFID tag 47 (not shown in FIG. 6) includes an antenna that may, or may not, be coupled to an integrated circuit chip or chip that can store or contain additional product information, tracking information, shipping information or any other desired product information. In operation, the processor, powered by the power source, provides a signal that is transmitted by the transceiver. The transmission energy of the signal communicated by the transceiver serves to inductively and communicatively couple the RFID tag 47 to the reader 26f. Reader 26f is essentially a small circuit board with circuitry for communicating with RFID tag 47. The circuitry usually includes its antenna, a controller or control circuit, and input/output circuitry for communicating with the autoconnect controller. When the RFID reader sends a signal, an electrical current is, in turn, inductively generated within the RFID tag antenna. The electrical current can serve as a "zero bit" to simply indicate the presence or absence of the RFID tag 47. Alternatively, the electrical current can power the chip, thereby allowing the additional information stored thereon to be communicated between the RFID tag 47 and the reader 26f. In one embodiment, RFID tag 47 records an indication each time the tag is read. In one embodiment, RFID tag 47 records and stores additional information from the system controller, including at least one of a patient identifier, an amount of dialysate or liquid administered, a date and time, and other helpful medical information.

The RFID tag 47 as illustrated is a passive tag, which includes no internal power source and instead is inductively powered and interrogated by the reader. In application with the present disclosure, RFID tag 47 can alternatively be a semi-passive device that includes a battery that is printed onto the substrate. The addition of the printed battery power source allows the antenna to be optimized for communication, as opposed to current generation. In another embodiment, the RFID tag can be an active tag that includes a long-life battery, one or more integrated circuits, display elements, storage elements, etc.

In some embodiments, the RFID tag 47 includes a transponder that operates at a relatively low frequency, about 125 kHz to about 134.2 kHz, or from about 140 kHz to about 148.5 kHz, and having a read range of as low as about one inch. A high frequency transponder typically operates at about 13.56 MHz with a read range of up to a meter. Further, transponders may even operate at an ultra-high frequency, such as 433 MHz, or typically between about 868 MHz to about 928 MHz, with a read range of about 3 m or beyond, such as those used for electronic toll collection and the like. In the present application, small, low frequency RFID tags with very short range are preferred, so that each tag is identified within its channel or range on the shuttle or other part of an autoconnect system. These ranges will preferably be less than one inch, in the range of about 20-25 mm. The reading range depends on the design of the reader or interrogator and can be kept short.

For purposes of the present disclosure, and regardless of physical configuration, an RFID tag includes any device configured to communicate information via radio waves transmitted at frequencies of about 100 kHz or higher. In fact, the operating frequencies of individual tags can be considered a secondary consideration given that the overall structures of typical tags are very similar. The RFID tags allow positive identification of each bag or container whose tag is placed into the shuttle. With this technique, the autoconnect controller, or the controller for the dialysis or other system, will know whether the placement made is correct and incorrect and notify or alert the operator or other personnel when an incorrect placement is made.

The above discussion focused on placing the containers of dialysate fluid, and their tubing and connectors, and automatically identifying the containers using RFID tags. It is clear from the above discussion, that other positive techniques may be used for identification, such as bar code labels or indicia on the tubing ends, and a bar code reader on the autoconnect device. Still other techniques may be used, such as i-buttons from Maxim Integrated Products, Sunnyvale, Calif. An i-button, similar to an RFID, is an integrated circuit with a unique identification, contained in a small, flat, metallic package. An i-button identification circuit usually requires touching to an i-button reader, but the principle of automatic and unique identification is similar to that used with a bar code or an RFID tag. It will also be obvious to those with skill in the art that the autoconnect device may be operated with no automatic identification feature, such as RFID tags or barcodes. Identification of the fluid dispensed may be made manually or by entering a information, such as a code, manually into a computer for tracking patient care.

Making Connections and Preserving Sterility

Figure 7:
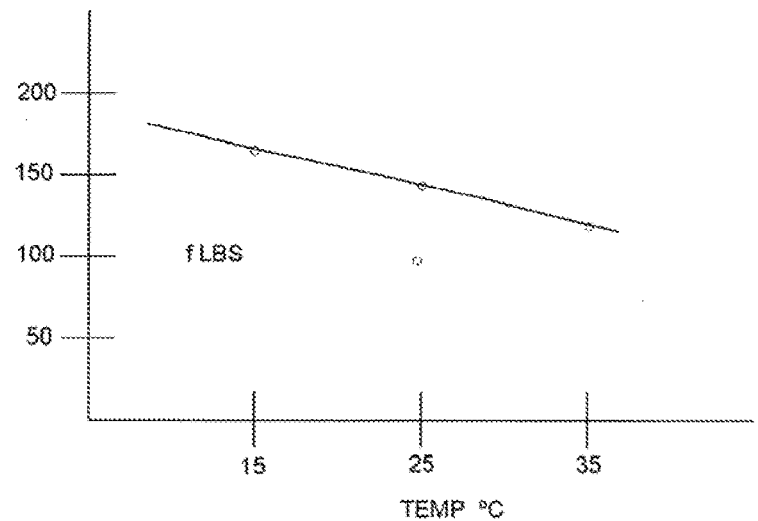
FIG. 7 graphs experimental results for the force needed for connecting containers of fluid.

Once the tubing is in place, the tubing is connected so the fluid in the containers can be dispensed or otherwise distributed or used. FIG. 7 illustrates graphically the problem in connecting bags of dialysis solution to the disposable cassette. The upper line with three points represents testing at different temperatures, while the lower line represents testing with an improved spike design. The force required for connecting four bags at room temperature, 25C, was about 140 lbs, or about 35 lbs force for each connection, which connections are of course made by hand, one at a time. At cooler temperatures, 15 C, the force for all four was about 160 lbs, or about 40 lbs force each, while at 35 C, the force dropped to about 120 lbs, or about 30 lbs force each. Even with the improvement of a stepped spike, as discussed for FIG. 8A below, the force required is still about 80 lbs, or about 20 lbs force for each connection.

Figure 8A:
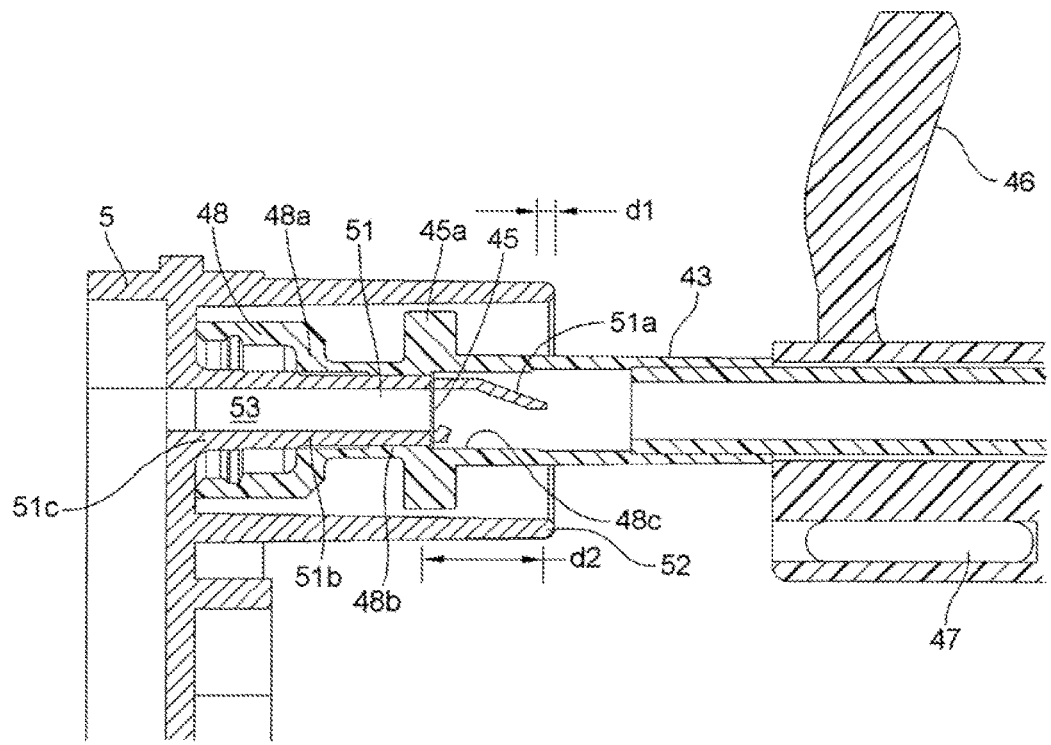
FIGS. 8A, 8B and 8C are a cross-sectional views of engagement between a containers of fluid and spikes, such as those from a pumping cassette.

FIG. 8A depicts the improvement in the spikes discussed above and also illustrates a technique used to insure that the connection between the disposable cassette and the tubing remains sterile. In this cross sectional view, tubing 43 with RFID housing 46 has been placed in position and membrane seal 45 has been penetrated and broken by hollow spike 51 of the disposable cassette port 52. The outer diameter of the distal portion 51a of the spike is less than the outer diameter of the spike main portion 51b, which may be slightly less than the diameter of spike proximal portion 51c. In addition, tubing end connection 48 may include three stepped portions, distal portion 48a with a larger inner diameter, mid-portion 48b with a smaller inner diameter, and proximal portion 48c with a larger inner diameter, which provides clearance for material from the penetrated seal to fold or hinge out without occluding the lumen and without requiring additional force to complete the penetration.

Spike 51 is contained within port 52. Spike 51 includes an inner lumen 53 so that when spike 52 penetrates membrane 45, a fluid connection is established between the dialysate solution bag tubing 43, and disposable cassette 5. The parts are designed so that the connection between sterile parts is made before the membrane seal of the tubing is broken, thus preserving sterility of the connection. The spikes are preferable a relatively hard plastic, such as acrylic, polycarbonate, or acrylonitrile-butadiene-styrene (ABS). Cyclic-olefin co-polymers (COCs), especially those blended with ULDPE, may also be used for the cassettes and spikes. See, e.g., U.S. Pat. No. 7,011,872, assigned to the assignee of the present patent, and which is hereby incorporated by reference.

The distal portion 51a of spike 51 does not extend beyond the outer rim of port 52, i.e., the spike is shrouded within the port. In this embodiment, port 52 extends a distance $d_1$ beyond spike 51 and spike distal portion 51a. This helps to prevent inadvertent touching and contamination of the spike after the port cap is removed. When tubing end connection 48 is seated within port 52, the distal portion 51a of the spike extends within tubing 43 for a distance $d_2$.

Spike distal portion 51a, as shown, has a smaller outer diameter than spike mid-portion 51b. As noted above, tubing connection 48 inner portion 48a has a larger inner diameter. When tubing 43 is connected to port 52, spike distal portion 51a with a small outer diameter encounters connector portion 48a with a larger inner diameter. In this embodiment, and as seen in FIG. 8, the outer diameter of the spike portion 51a is less than the inner diameter of connector inner portion 48a, allowing the spike to pass through without interference. Upon further insertion, when connector inner portion 48a encounters spike mid-portion 51b, a seal is made between them just before the spike tip penetrates seal membrane 45. After penetration, spike mid-portion 51b seals against tubing mid-portion 48b. In addition, an outer seal is made between tubing proximal portion 48a and spike proximal portion 51c at the entrance to the tubing, i.e., the entrance to tubing portion 48a.

This arrangement of a stepped spike and stepped connector tubing minimizes insertion forces while simultaneously minimizing opportunities for contamination of the connection parts. It will be recognized that other spikes may be used, such as tapered, non-stepped spikes, as well as tapered, non-stepped spikes with a leading edge on one portion of the spike arc. It will also be recognized that some spikes may have a sharp edge, while others will be blunt. Using a blunt edge helps to prevent injuries. In the present embodiment, designed for no contact with a person using or operating the autoconnect system, sharp edges are preferred, for minimizing the force necessary to make the tubing connections.

Figure 8B:
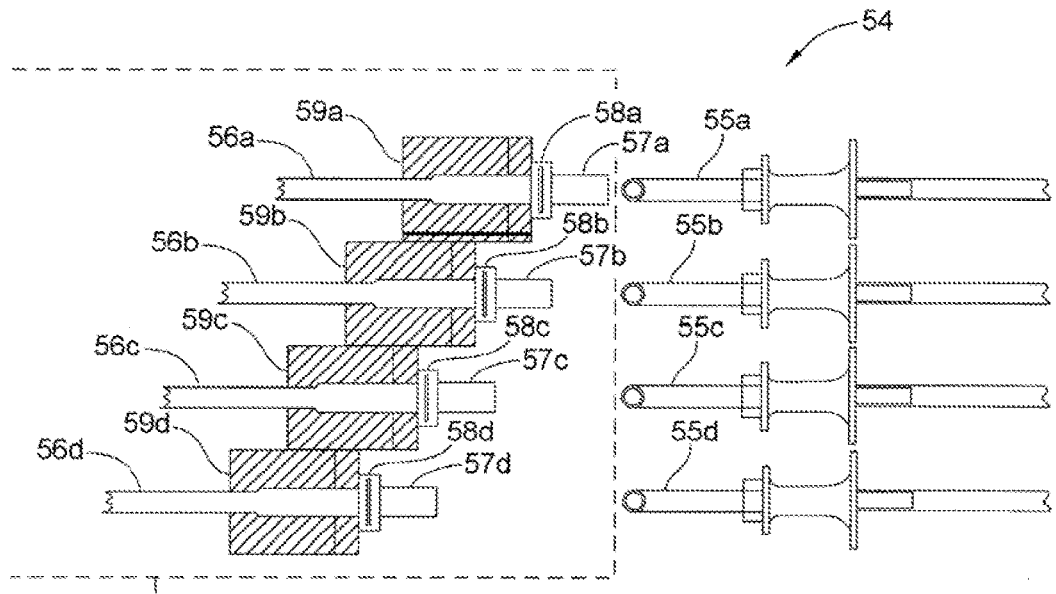
Figure 8C:
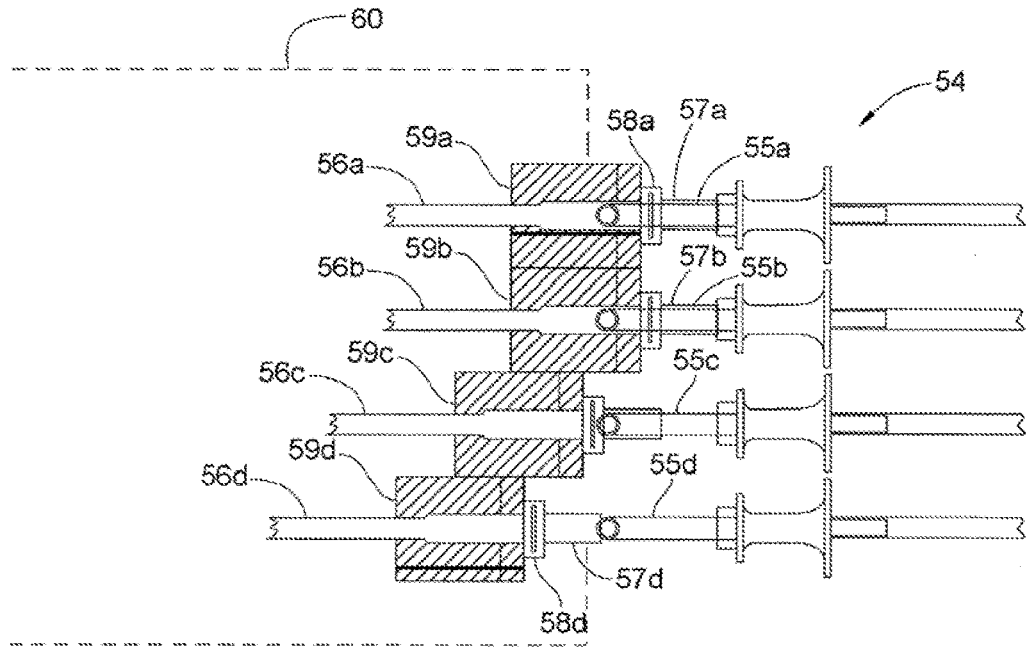

FIGS. 8B and 8C depict an autoconnect mechanism in which the tubing tips approach the cassette 54 and spikes 55a-55d for sequential spiking. In this embodiment, shown with the tips of four containers of medical fluid, the autoconnect mechanism has four independently-moving tips, 57a-57d, from four containers with outlet tubing 56a-56d. Each tip has a membrane or seal 58a-58d for spiking by the spikes 55a-55d. The tubing and tips are mounted in independently-moving mounts 59a-59d on a stationary platform 60. As discussed below with respect to FIGS. 19-21, separate movement for each mount may be provided by suitable devices, such as solenoids, air cylinders, electric motors, or even hydraulic cylinders. The mounts may be mounted on a shuttle or to tracks on the autoconnect frame directly. In this embodiment, the shuttle does not translate, but instead each device provides the separate back-and-forth movement described for the shuttle. Note that in FIGS. 8B-8I, the spike shrouds, the outer part of the ports, are not shown for clarity.

FIG. 8B depicts the four tips 57a-57d and mounts 59a-59d approaching spikes 55a-55d in a sequential manner. In practice, only one tip may be advanced at a time. Preferably only one spiking connection is made at a time. As seen in FIG. 8C, the top two tips, 57a, 57b and membranes 58a, 58b, have been spiked, one at a time, by spikes 55a, 55b. The third tip, 56c, is approaching the third spike 55c, and the fourth spike will be next. By using sequential spiking, the total force required for penetration of the membrane by each spike is spread over four time sequences, rather than all at once. Thus, the motor, cylinder, or solenoid that advances each mount may be smaller, since it needs only enough force to penetrate one seal, about 20-25 lbs force. Alignment of the mounts with the spikes may also be easier, since each mount, in its own channel or pathway, need only align with a single spike. Even though there may be a plurality of mounts and pathways to align, there are just as many to align in embodiments with a translating shuttle.

The above discussion focused on automatically making the connection between containers of dialysate fluid and the inlet ports of a disposable cassette. By analogy, the same technique with suitable geometries may be used for automatically making sterile connections between other containers of fluid and other dispensing or pumping systems. As previously noted, disposable cassettes may have their connection ports on the top of the cassette, or on the side. Of course, placement of the ports on the periphery of the pumping mechanism is preferable, whether top, bottom, side, or on an edge of the top, bottom, or side. The same principles apply to other fluid container connections, such as bags of blood or blood substitute being connected to an inlet port for a blood transfusion machine, such as a cardiopulmonary pump, bypass pump, or auto-transfusion machine. Still other applications are also possible.

Making Sterile Connections Sequentially

Figure 8D:
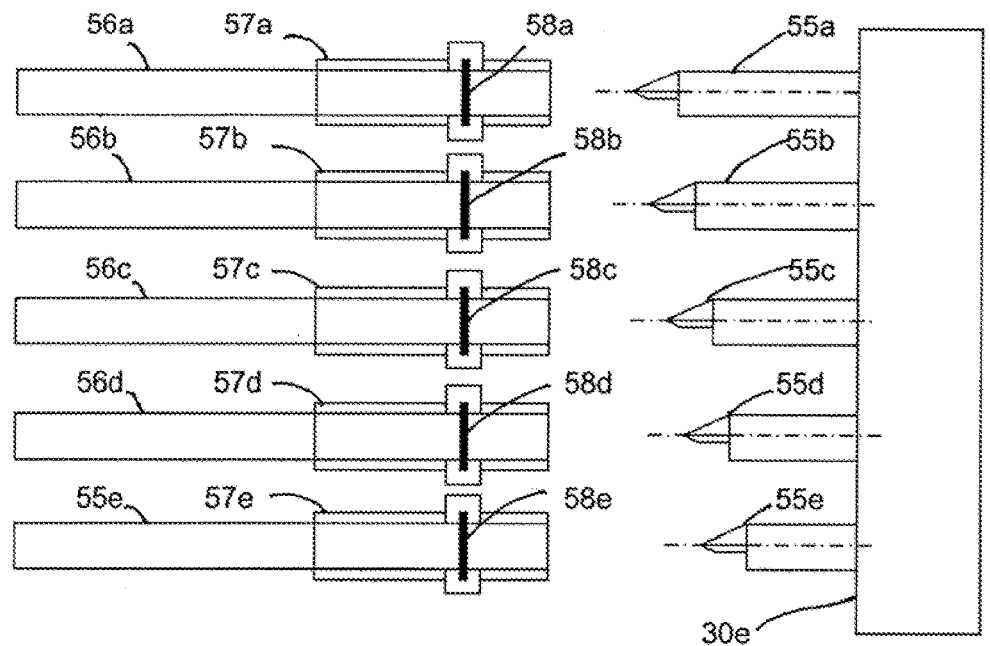
FIGS. 8D-8I depict sequential spiking of container membranes by spikes protruding different distances from a cassette in another cassette embodiment.

In another embodiment, the cassettes used to connect containers of dialysis fluid may have spikes that protrude different distances from the cassette. In this embodiment, the shuttle advances with a plurality of tubing ends, each tubing end and membrane arranged in a row, as shown in FIG. 8D. In this embodiment, spiked cassette 30e, the individual spikes protrude different distances, each preferably about 1/16 of an inch to about 1/2 inch more than the next, more preferably about 1/8 to 3/8 of an inch, most preferably about 1/4 inch. The difference is determined by the distance the shuttle must travel for one spike to penetrate the membrane until the membrane flaps have been turned and the tubing tip has moved beyond the narrowest portion of the membrane/spike interface. Five sets of tubing, 56a-56e have been arranged on the shuttle, each with its tubing tip 57a-57e, and membrane 58a-58e. The caps guarding the sterility of the connection have been removed, as described below.

Figure 8E:
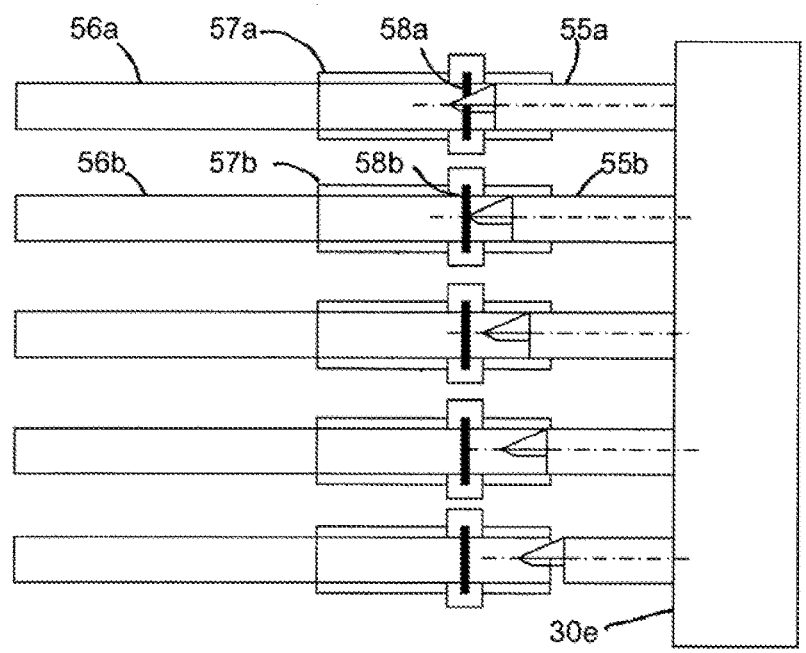
Figure 8F:
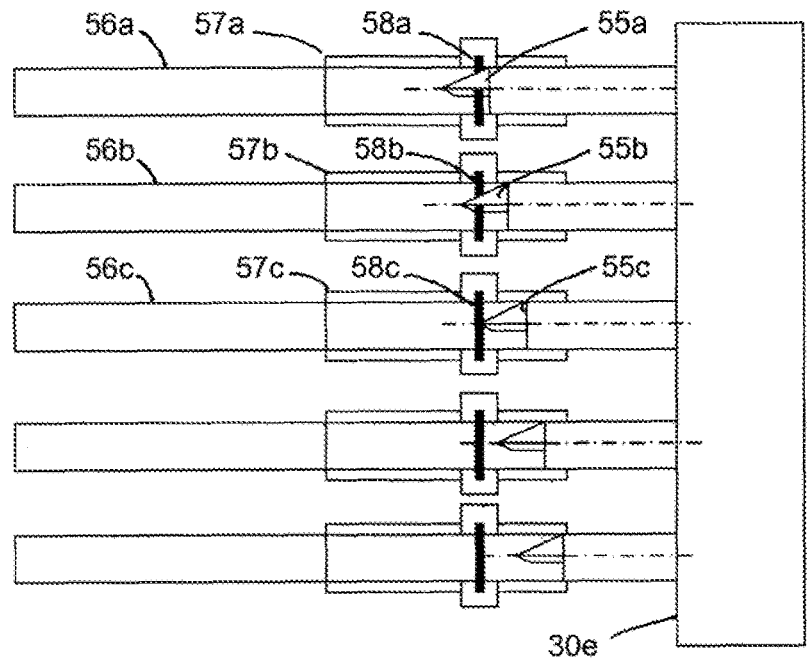
Figure 8G:
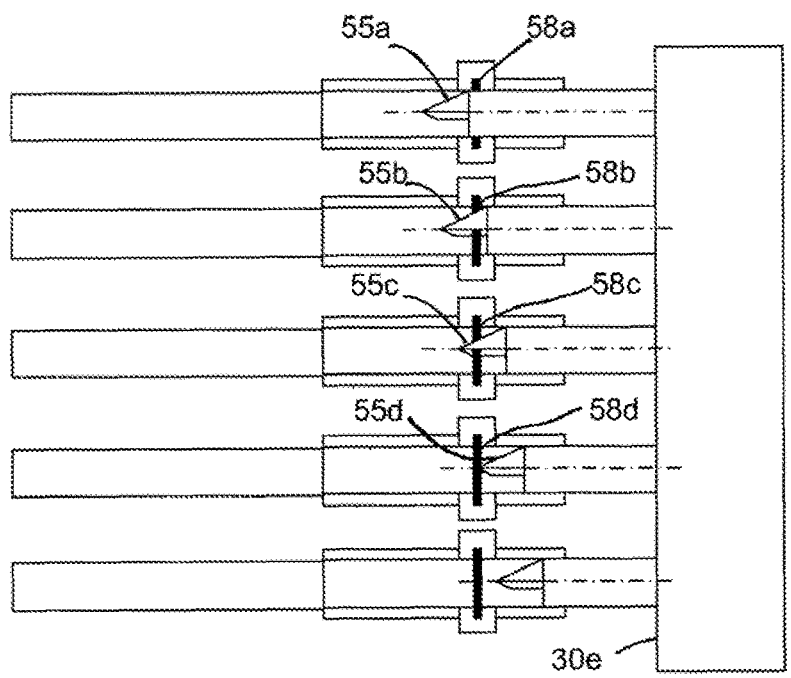

In FIG. 8E, the shuttle with all five sets of tubing has approached the cassette, and first spike 55a has penetrated first membrane 58a, while second membrane 57b has just touched spike 55b as the shuttle moves forward. In FIG. 8F, the shuttle and first membrane 58a have almost cleared first spike 55a, while second membrane 58b has just been pierced by second spike 55b. Depending on the clearance and the actual lengths used for the diameters of the spike, the force involved may be significant, and could cause stalling of the actuators used to advance the tubing, or could cause buckling of the shuttle or other mechanisms. This is the reason for protruding the spikes at different distances. In FIG. 8G, the shuttle has advanced further. First spike 55a has cleared membrane 58a, second spike 55b has almost completed penetration of second membrane 58b, and third spike 55c has just begun to penetrate third membrane 58c. Fourth membrane 58d has just touched fourth spike 55d. Thus, in FIG. 8G, the shuttle is providing sufficient force to handle two penetrations, although the force required for the second spike 55b to finish clearing membrane 58b may be minimal.

Figure 8H:
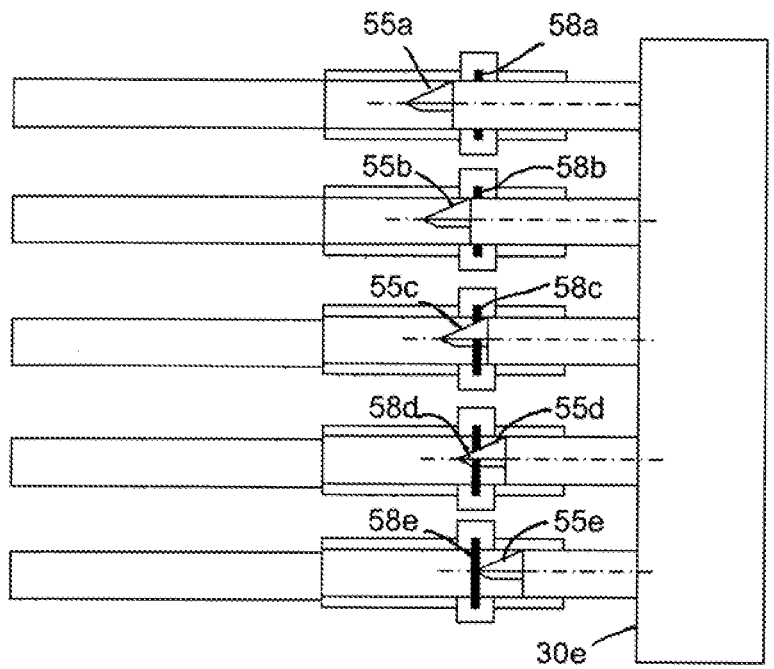
Figure 8I:
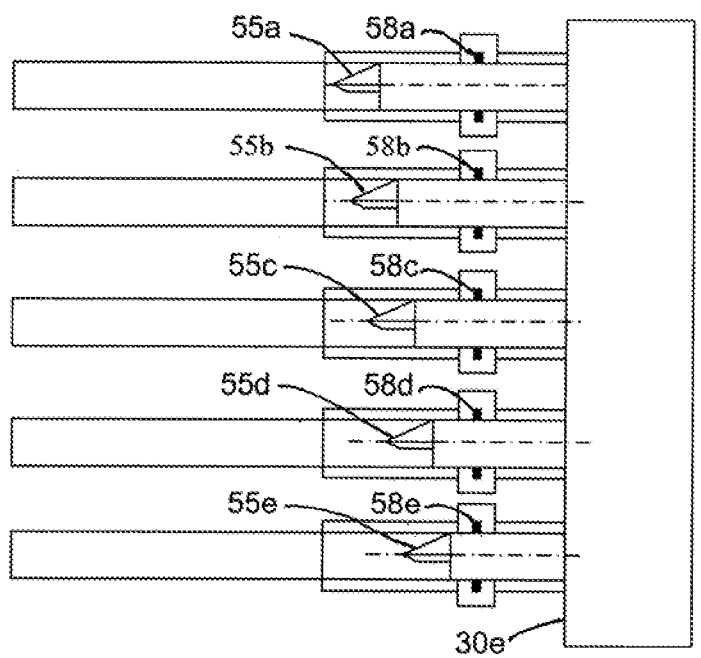

The sequence continues in FIG. 8H, in which first and second membrane 58a, 58b have cleared first and second spikes 55a, 55b. Third and fourth spikes 55c, 55d are moving through membranes 58c, 58d, while fifth membrane 58e has just reached fifth spike 55e. Finally, in FIG. 8I, each spike has cleared through its membrane and the dialysis machine is almost ready to begin its cycle.

Operation of the Fingers and Removal of the Caps

An important part of making the connections is the automatic removal of caps from both the tubing and the ports of the cassette or other pumping and dispensing mechanism. Automatic removal of the caps is an important part of the process because the caps, and the underlying ports and connections, may easily be touched and thus contaminated if the caps are removed by hand. Thus, as discussed above, special fingers are used to remove caps from both the product container tubing and from the ports of the pumping or dispensing machines, typically a disposable dialysis cassette.

Figure 9:
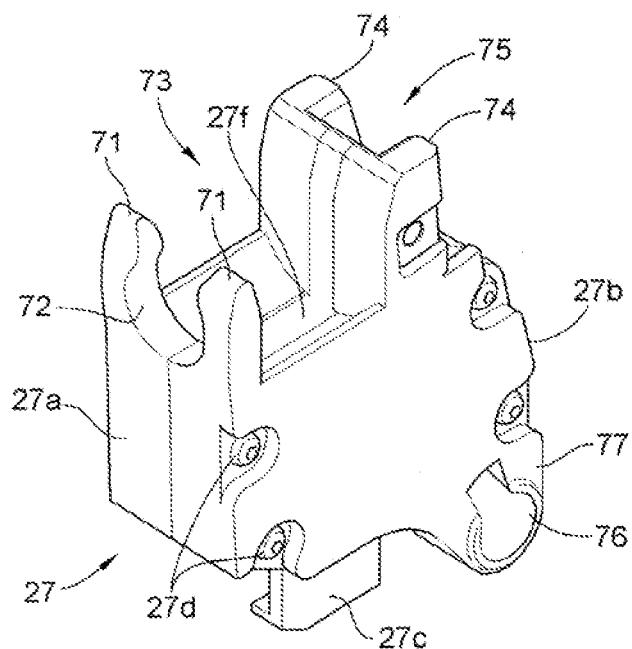
FIGS. 9 and 10 are rear and front perspective views of details of a first embodiment of rotating fingers for use in an autoconnect machine.
Figure 10:
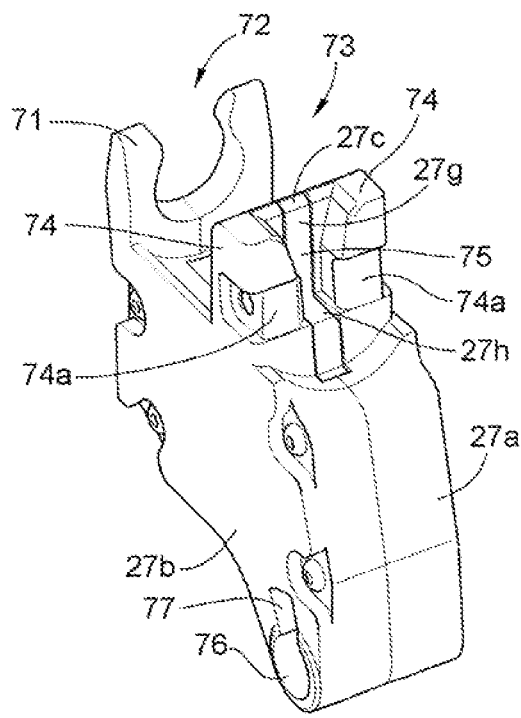
Figure 11:
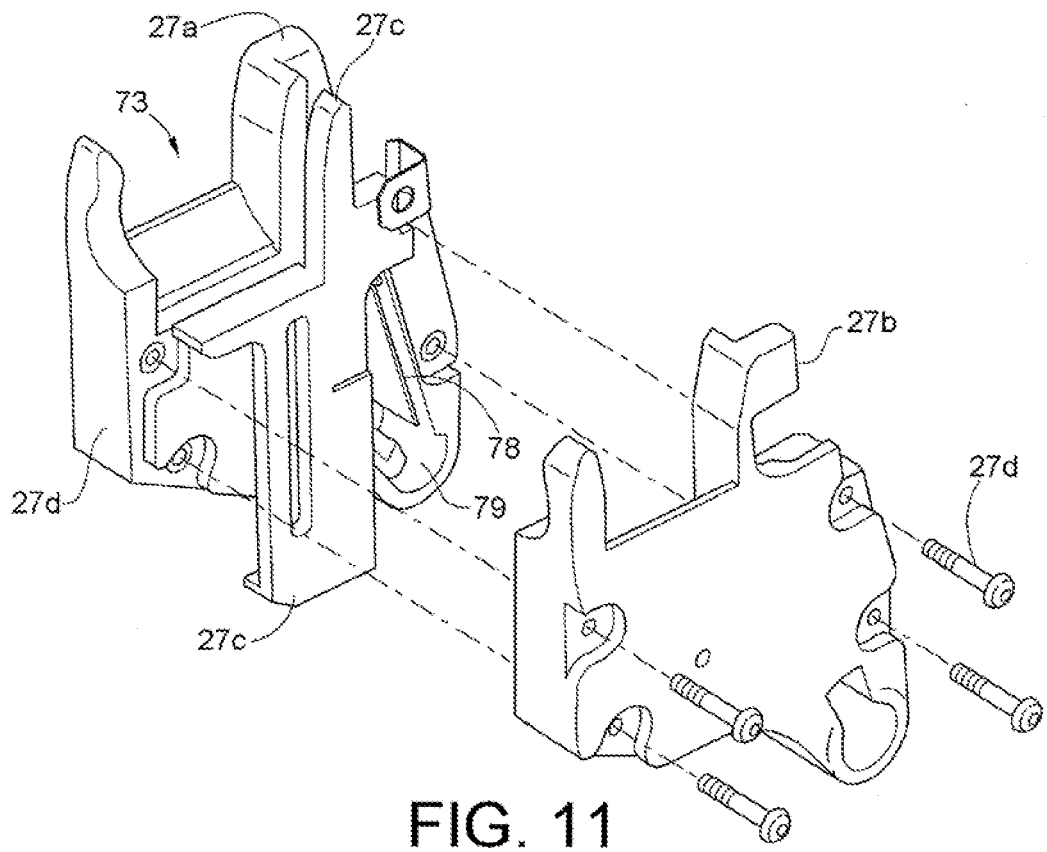
FIG. 11 is an exploded view of the embodiment of FIGS. 9 and 10.
Figure 12:
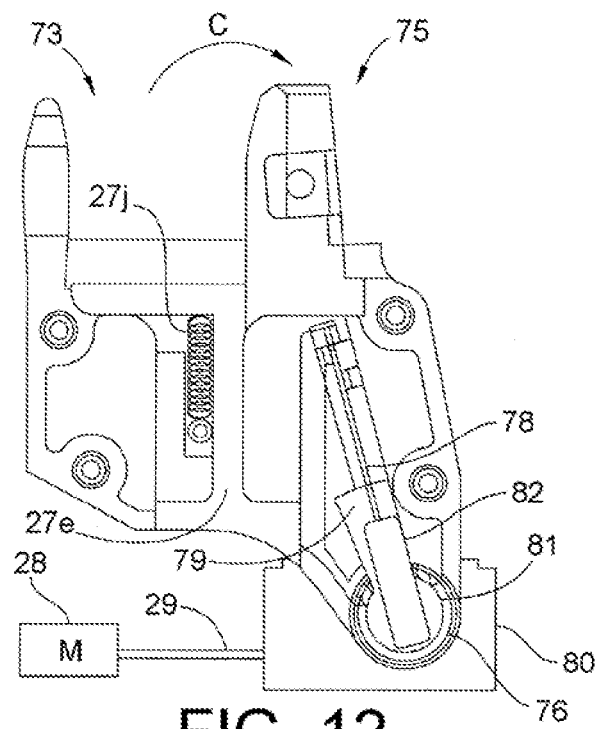
FIG. 12 is a side view of the embodiment of FIG. 9.

One embodiment of cap removal fingers is disclosed in FIGS. 9-14. FIG. 9 discloses a rear perspective view and FIG. 10 a front perspective view, of a finger 27 with left and right sides, 27a, 27b, a cap ejector plate 27c, finger 27 assembled with fasteners 27d. Ejector plate 27c is mounted within pocket 27 and travels via slot 27e within left and right sides 27a, 27b. In one embodiment, as shown in FIG. 12, a torsional spring 27j is mounted within finger 27 and under top surface 27f of the ejector to resist advancement of the ejector plate and to return it to the resting position shown in FIGS. 9-10. The top side of finger 27 includes a first pocket 73 with extended rails 71, the rails forming an orifice 72. Orifice 72 allows passage of tubing, as discussed above, but is smaller than the diameter of the cap for the tubing. The walls of rails 71 are curved, together forming about 290 degrees of a circle, i.e., the periphery of the cap, or the portion of the cap inside the outermost periphery, an inner periphery. This restraint allows the rails to retain the caps when the shuttle and tubing are retracted, as discussed above. The orifice is preferably at least about 180 degrees, and experiments have found that 290 degrees works well for removing caps. Other configurations with lesser coverage, such as several angularly spaced points, are also adequate for stripping the tubing cap from the tubing.

The top of finger 27 includes a second pocket 75, formed by extended rails 74 of left and right sides 27a, 27b. In this embodiment, the pocket 75 is formed by the rails 74 and by inserts 74a, spaced more closely than rails 74. The inserts are designed for grasping the center portion of a cap from a dispensing or pumping machine, such as a dialysis cassette. As noted above, fingers 27 grasp the stepped, protruding nipple from the dispensing or port cap. The interference should be sufficient so that the cap is retained between the inserts. In one embodiment, inserts 74a are sharp near the center, so that when the finger 27 is rotated and the shuttle translated into the nipple of the port or dispensing cap, the inserts cut into the nipple portion, grasping the nipple portion. When the finger begins to rotate in reverse, the cap remains captive and is pulled away from the port. Also visible from both the top and bottom of finger 27 is an ejector plate 27c contained within the finger. Finger 27 includes a through shaftway 76 with a notched portion 77. A shaft rotates within the shaftway to rotate the fingers and to advance and retract the ejector plate. When the caps have been removed as discussed above, and are resting in pockets 73, 75, the finger is rotated and the ejector plate is advanced to eject the caps, all without touching and contaminating the tubing or the ports.

As seen in FIGS. 11-12, a shaft 81 actuated by motor 28 (see FIG. 1), input shaft 29 and gear train 80 extends through finger 27 and shaftway 76. Also contained within each finger 27 inner space 79 is a leaf spring 78, the leaf spring mounted against pin 82. Finger 27 can rotate relative to shaft 81, its travel limited by pin 82. The leaf spring 78 biases finger 27 to the back position, as shown in FIG. 12. There is sufficient clearance within space 79 so that pin 82 and leaf spring 78 can rotate back and forth, which limits travel, but also allows rotation of finger 27 in the general direction of the arrow C as shown, toward the cassette. When the shuttle is advanced, finger 27 rotates as shown and as allowed by the pin. In one embodiment, this is about 5 degrees. This is sufficient to allow the inserts 74a to grasp the port cap from a dialysis cassette port. Once rotation has taken place, the shuttle prevents reverse movement or rotation of finger 27. However, leaf spring 78 is engaged by rotation of the finger, and now urges finger 27 to rotate back, in the direction opposite arrow C. Thus, when the shuttle is reversed, and translates back, away from the cassette, finger 27 does indeed rotate away from the cassette, while gripping the port cap in second pocket 75 and removing it. The finger motor will cause the port cap to fall out as the finger is rotated down, out of the way. As discussed above, the cap from the tubing is held in first pocket 73.

Figure 13:
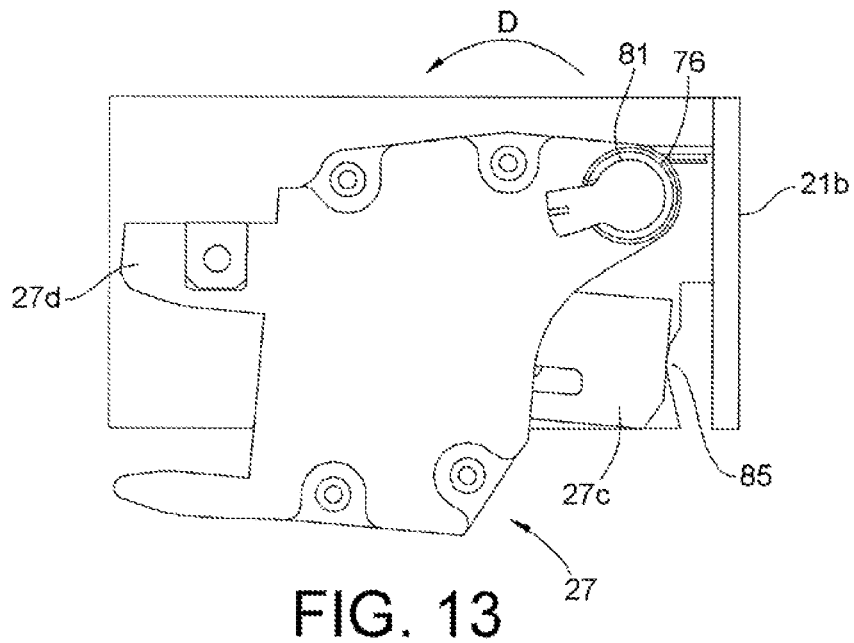
FIGS. 13-14 are additional views showing the functioning of the rotating fingers.
Figure 14:
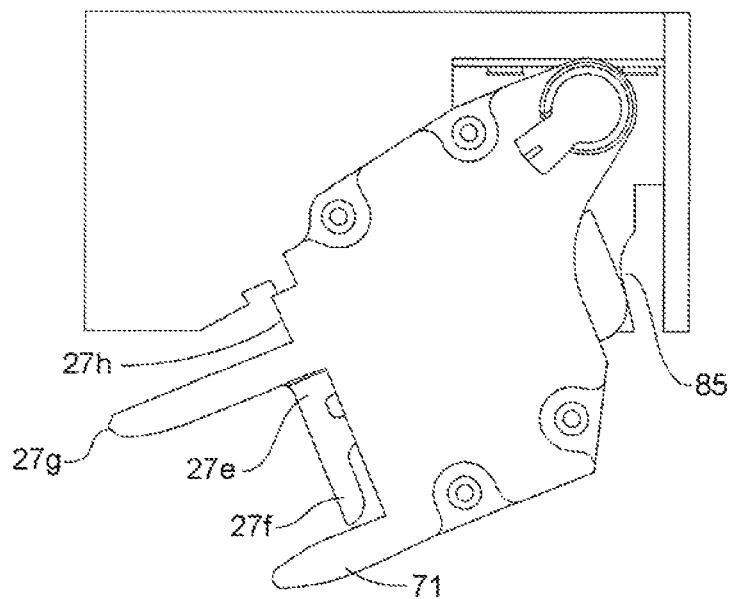

The caps have now been removed from the tubing and the port, and are disposed of before making the connections between the tubing and the port. FIGS. 13-14 depict rotation of finger 27 about shaft 81. After the shuttle has been translated back, away from the fingers, the fingers may be rotated downward to remove the caps. Output shaft 81 from gear train 80 rotates the fingers to actuate the ejector plate 27c and eject the caps from pockets 73, 75. Gear train 80 may include bevel gears on the shafts to turn motive power from motor 28 and input shaft 29 ninety degrees to rotate output shaft 81. In the alternative, a worm on the input shaft and a worm gear on the output shaft, or crossed helical gears will also work.

As finger 27 is rotated counterclockwise in the direction of arrow D beyond horizontal, ejector plate 27c will encounter protrusion or cam surface 85 on back wall 21a of the autoconnect frame. The interference will cause the bottom edge of ejector plate 27c to bear against cam surface 85, advancing ejector plate 27c through finger 27. As seen in FIG. 14, the top portions of the ejector plate, including a slide channel 27e top portion and top surface 27f, and a top ejector rear portion 27g, now protrude from the finger 27. Top surface 27f will eject a cap from pocket 73 and top portion 27h will eject a cap from pocket 75. The fingers will remain in the down position, out of the way, during therapy.

Overall Operation of an Autoconnect Device

Figure 15A:
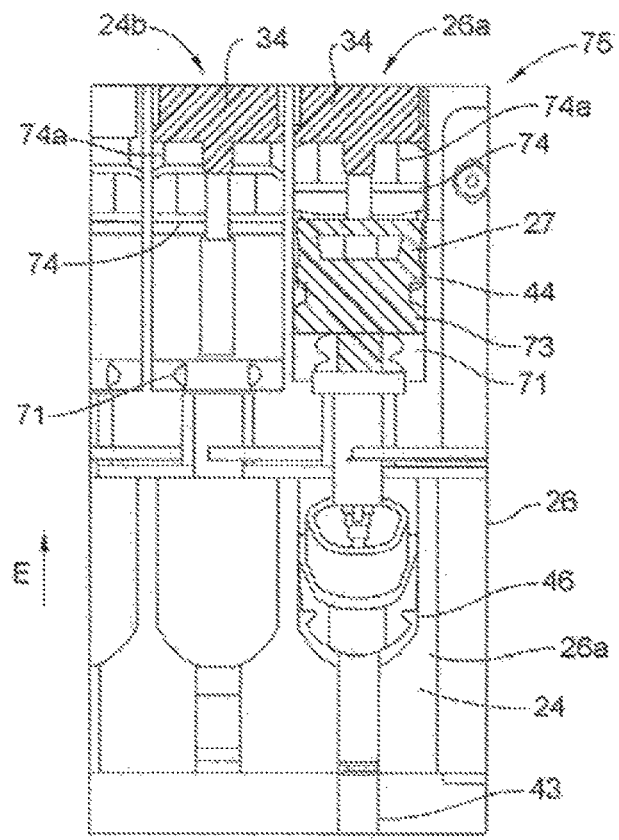
FIGS. 15A, 15B, 16A, 16B, 17A and 17B depict operation of an autoconnect machine.
Figure 15B:
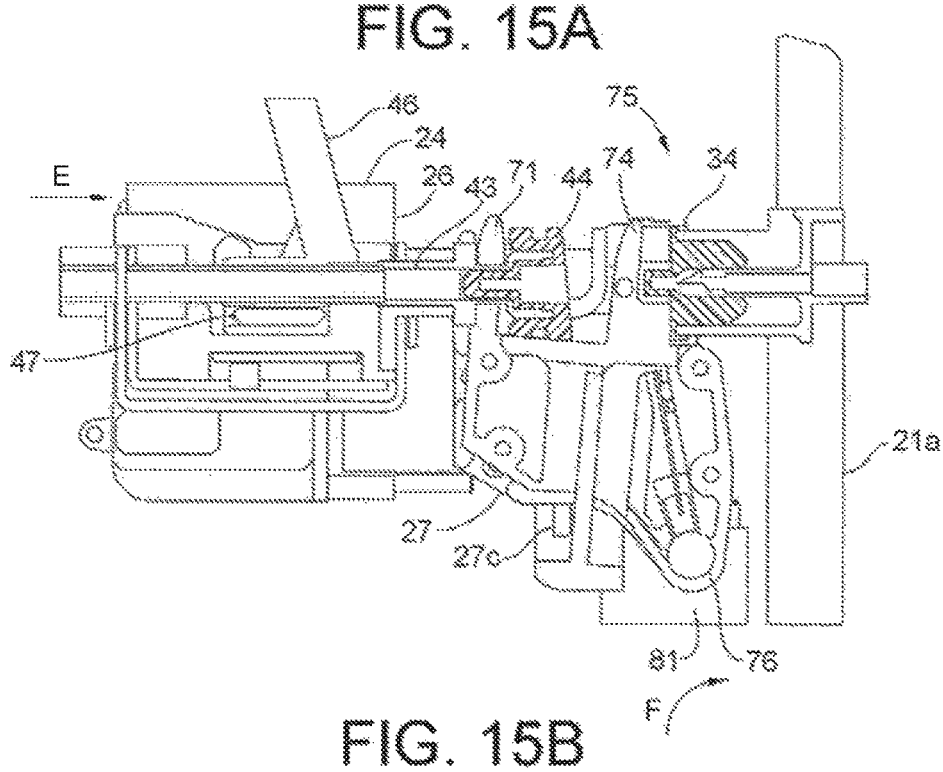

The above description may be better understood by disclosing sequential views of the operation. FIGS. 15-17 lead this discussion, and FIG. 18 provides a flow-chart version of the autoconnect process. In FIG. 15A and FIG. 15B, tubing 43 has been placed in a shuttle 24 channel 26a of central area 26, along with RFID housing 46 and RFID tag 47. For comparison in FIG. 15A, an unoccupied channel 24b, adjacent occupied channel 26a is shown, along with the fingers corresponding to the used and unused channels. Shuttle 24 has been advanced in the direction of arrow E, causing slight rotation of finger 27, but only the finger corresponding to channel 26a. This slight movement can be seen by the fact that rails 71, 74 of finger 27 in channel 26a have been advanced slightly.

As can be seen in FIG. 15B, this causes a slight clockwise rotation of finger 27 in the direction of arrow F and in the general direction of frame back wall 21a. As noted, finger 27 rotates about shaft 81 within shaftway 76. Returning to FIG. 15A, the slight rotation is sufficient for second pocket 75 to capture port cap 34, the port cap to the port and corresponding to shuttle channel 26a. This can be seen in top view FIG. 15A, as the port cap 34 is captured between extended rails 74. In contrast, in adjacent channel 24b, extended rails 71, 74 have not been advanced in the direction of arrow A, and extended rails 74 are not adjacent port cap 34 in the adjacent channel 24b.

Figure 16A:
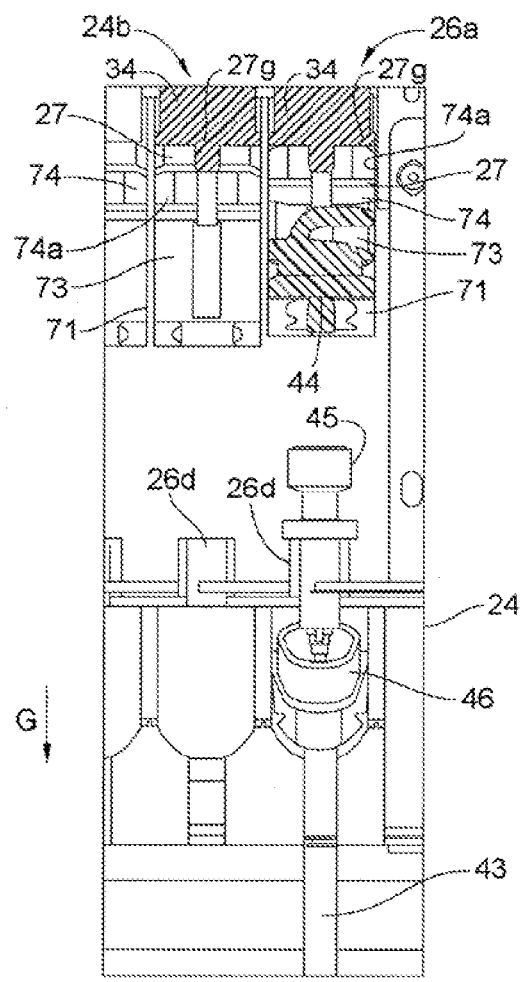
Figure 16B:
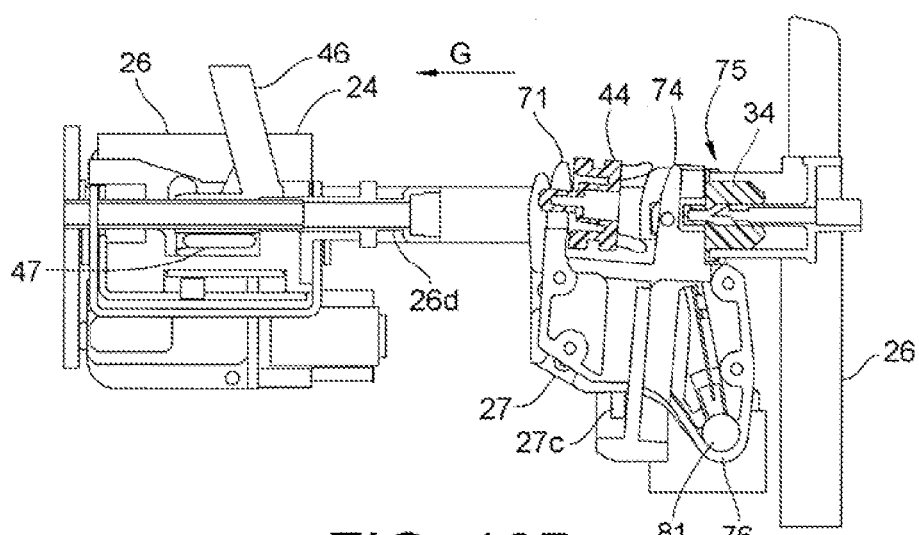

In FIGS. 16A and 16B, shuttle 24 has retracted in the direction of arrow G, away from frame back wall 21a. In channel 26a, but not in channel 24b, tubing cap 44 has been removed from tubing tip 45, the tubing cap retained in pocket 73 of finger 27. Finger 27 in channel 26a remains rotated rearward, as it was in the previous figures. Extended rails 71, 74 in channel 24b are thus offset from extended rails 71, 74 of finger 27 in channel 26a. Port cap 34 has been captured in pocket 75 of finger 27, but only in channel 26a, not in channel 24b.

Figure 17A:
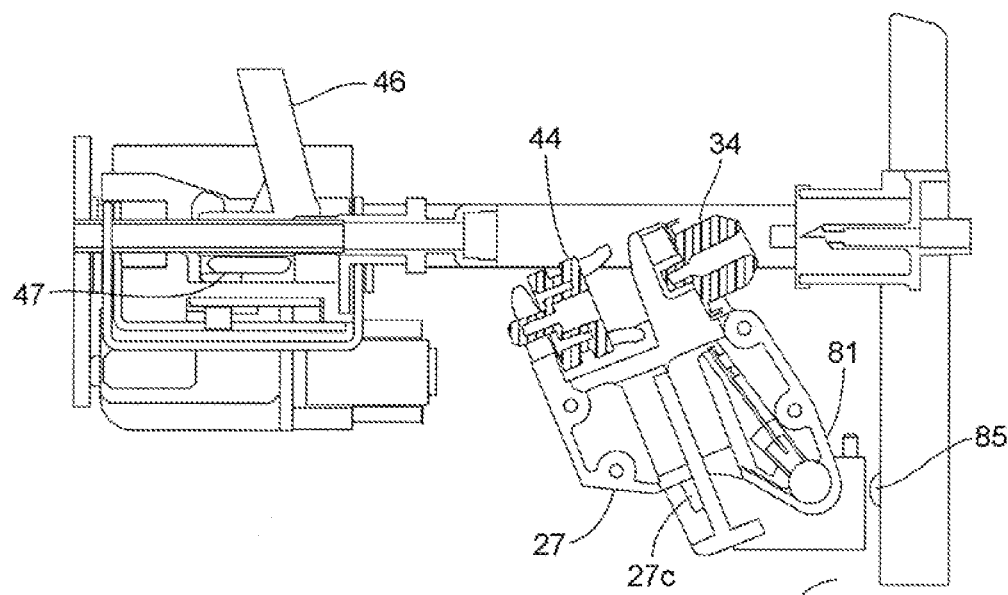
Figure 17B:
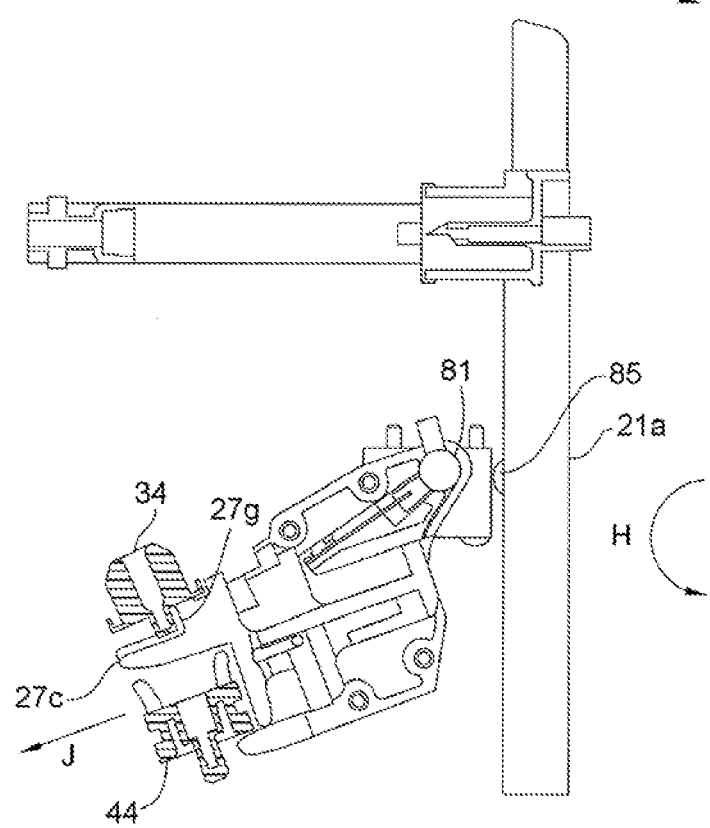
Figure 18:
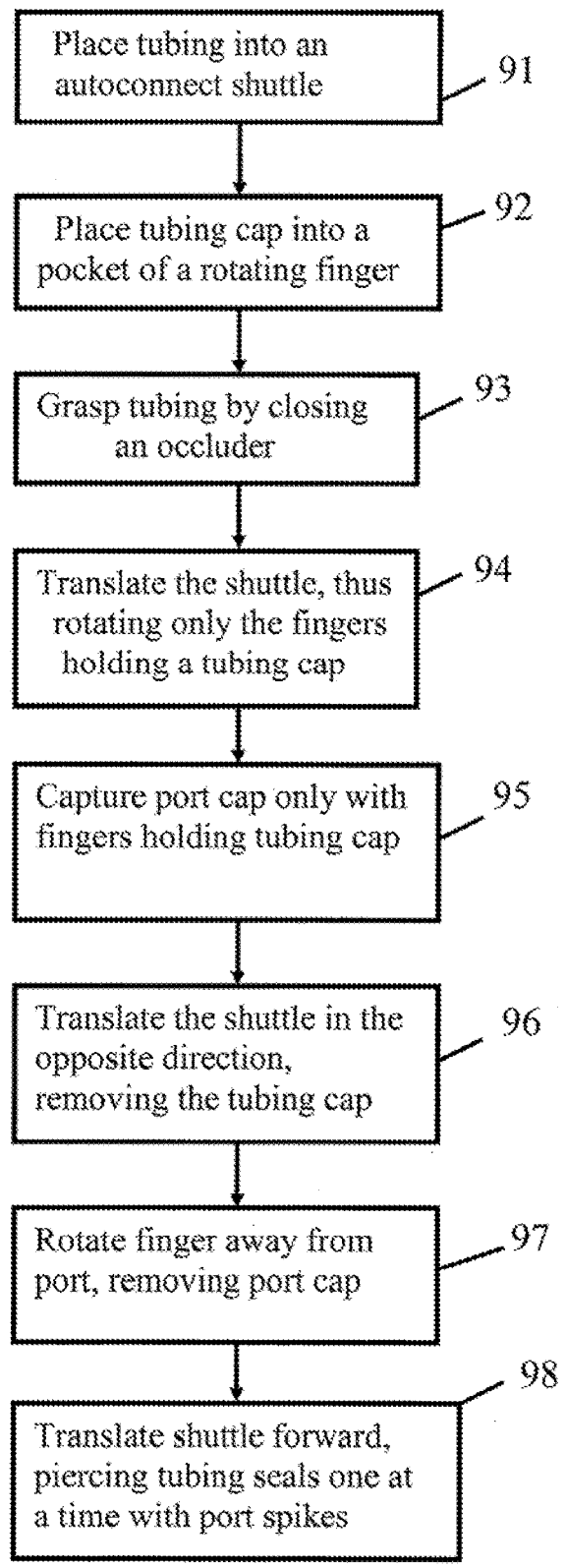
FIG. 18 is a flowchart for a method of operating an autoconnect machine.

FIGS. 17A and 17B illustrate the next two sequences in automatically removing the caps. Shaft 81 rotates counterclockwise in the direction of arrow H, causing finger 27 to also rotate. As the rotation continues, ejector plate 27c encounters a protrusion or cam surface 85 on back wall 21a, causing ejector plate 27c to advance within finger 27 in the direction of arrow J, causing the ejector plate to push caps 34a, 44 out of pockets 73, 75 and ejecting them from finger 27. After the caps are removed, and after therapy is concluded, the fingers can be rotated clockwise back to their normal position, opposite the direction of arrow H. In this embodiment, all the fingers are rotated, including fingers with no caps. In other embodiments, gearing or other power is arranged to engage only the fingers corresponding to channels with tubing.

The process as described above, for a method or process of automatically connecting tubing, is easily visualized with the aid of the flow chart of FIG. 18. The first step 91 is to place the tubing into an autoconnect shuttle. A cap of the tubing is then placed 92 into a pocket of a rotating finger. The tubing is grasped by closing 93 on the tubing with a holder or occluder. The shuttle is then translated 94 a short distance forward, moving forward tubing and the cap, along with the shuttle. This movement is sufficient to cause a slight rotation only of a finger which holds a tubing cap. When the finger is rotated, it captures 95 a port cap from a disposable cassette, or other dispenser, which will be connected to the tubing.

The shuttle is now translated 96 in the opposite direction, away from the cassette, removing the tubing cap, which is held in a pocket of the rotating finger. The finger is now rotated 97 away from the cassette, removing the port cap. The rotation may continue until the top of the rotating finger is below horizontal, and causing the caps atop the rotating finger to fall away. In one embodiment, the rotating finger includes an ejector plate that is actuated by a cam surface on the back wall of the autoconnect frame. After removal of the caps, the shuttle is translated forward 98, piercing the tubing seal with spikes in the cassette port, one at a time in sequence because of the different spike protrusions. It is understood that this process is applicable to tubing from containers of a number of other liquid products, and may be used for automatically connecting to dispensers or pumping stations for the products.

Alternative Mechanisms for Shuttle Translation

The above descriptions have used an electric motor and lead screws to translate the shuttle, i.e., to move the shuttle back and forth in the direction to and from the disposable cassette, or other pumping or dispensing mechanism. Many other techniques and equipment may be used, a few of which are described in FIGS. 19-21.

Figure 19:
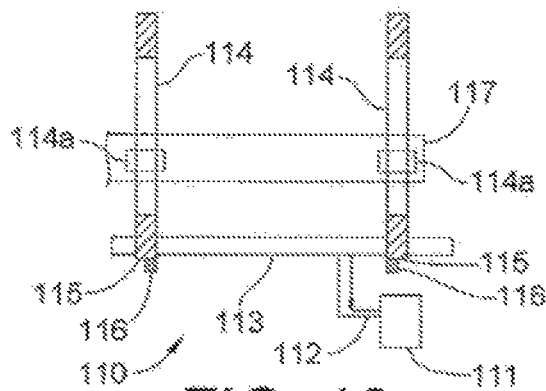
FIGS. 19-21 disclose alternative mechanical equipment for operating an autoconnect device.

A ballscrew, with a rotating nut and traveling balls, may also be used to translate the shuttle back and forth. FIG. 19 schematically depicts the use of ball screws in shuttle transport system 110. The shuttle transport system includes an electric motor 111 and its controller, suitable power transmission elements 112, and a power divider 113, to split power from the motor and drive two ballscrews 114. Each ballscrew is driven by a suitable interface 115 from power divider 113. Each ballscrew may also include an encoder 116 for sensing the shaft or ballscrew rotation, and thus the position of the shuttle 117. The shuttle 117 is mounted to the rotating nuts 114a of the ballscrews 117. As the ballscrews are rotated, the nuts translate or move back and forth, as does the shuttle. Other sensors may be used to determine shuttle position.

Figure 20:
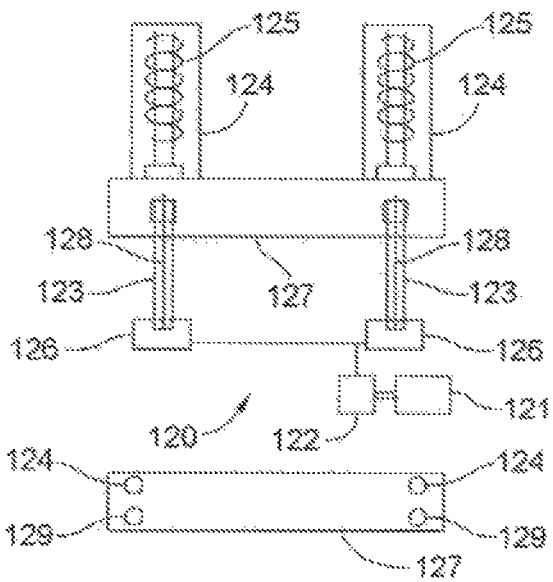

Pneumatic cylinders may also be used to move the shuttle back and forth, as shown in FIG. 20, depicting pneumatic shuttle transport system 120. Air may be supplied from a building compressor or plant air. For home use, however, a small air pump 121 and a suitable pressure regulator 122 and controller may be used. In this embodiment, shuttle 127 is mounted on the traveling or rod portions 124 of air cylinders 123. The cylinders may be single acting with an internal return spring 125 within the cylinder, or may be double-acting cylinders, for which no return spring is necessary. Air cylinders 123 are mounted on mounts 126, mounted on the autoconnect frame, for steady motion. The pneumatic driving system also includes a linear position sensor including linear transducers 128 mounted to the shuttle and the frame and sending out signals to the system controller of the position of the shuttle. As seen in the lower view of FIG. 20, the pneumatic system may include the pneumatic motive system as described, with shuttle 127 moved by air cylinder rods 124. Mounting rods or sliders 129 may also be used in parallel with the air cylinders.

Figure 21:
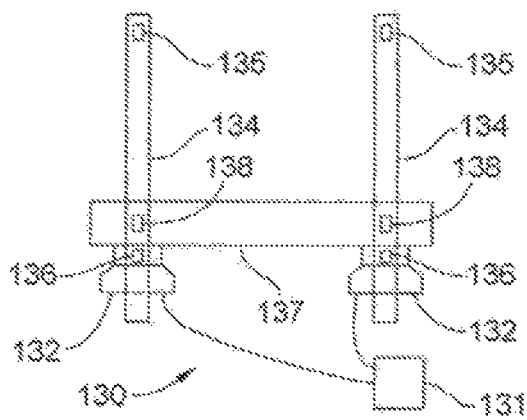

Because of the relatively short distances involved in translating the shuttle, it is also appropriate to use solenoids, preferably electric actuated, to translate the shuttle. FIG. 21 depicts an application in which solenoids are used in a solenoid transport system 130. Of course, more than one solenoid may be used, but solenoids with more than one position change are now available, such as the multi-position models from Guardian Electric Mfg. Co., Woodstock, Ill., U.S.A. In this application, shuttle 137 is mounted on the plungers 136 of solenoids 132. The solenoids are powered and controlled by controller 131. In addition, the position of the shuttle is noted by at least one hall effect sensor 138 on the shuttle and magnets 135 mounted at appropriate locations along the path of the shuttle. Other position sensors may also be used. In addition, the shuttle may use sliders 134, above or below the plane of the plungers, for travel in addition to the plungers of the solenoids mentioned above for the pneumatic shuttle transport system.

In addition, other mechanical or fluid power devices may be used for shuttle transport, such as hydraulics. Hydraulics are typically not used for medical devices because of certain aspects of hydraulic fluid. However, the autoconnect device uses relatively low power, and non-toxic hydraulic fluids are now available, such as the UCON™ FDC 300 and 400 grades from Dow Chemical. These fluids are approved for incidental food contact and may be safely used. A hydraulic system for shuttle transport would include at least a motor, a hydraulic pump, a reservoir for the hydraulic fluid, and control lines and systems for two-way movement of the shuttle.

Figure 22:
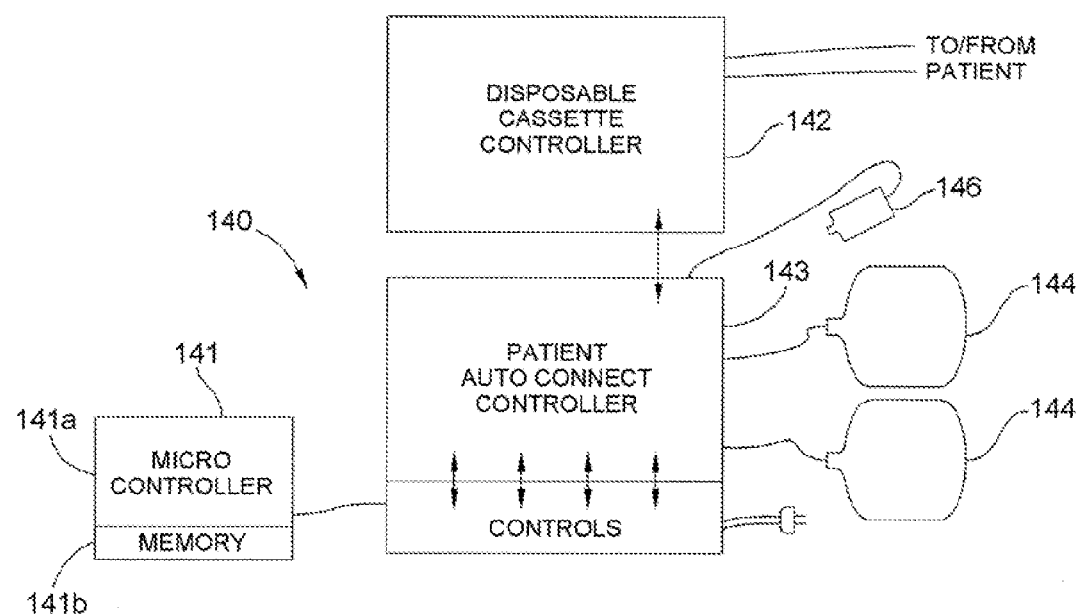
FIGS. 22-23 are schematic diagrams for a control system for operating an autoconnect machine, a pumping cassette, and a dialysis machine.
Figure 23:
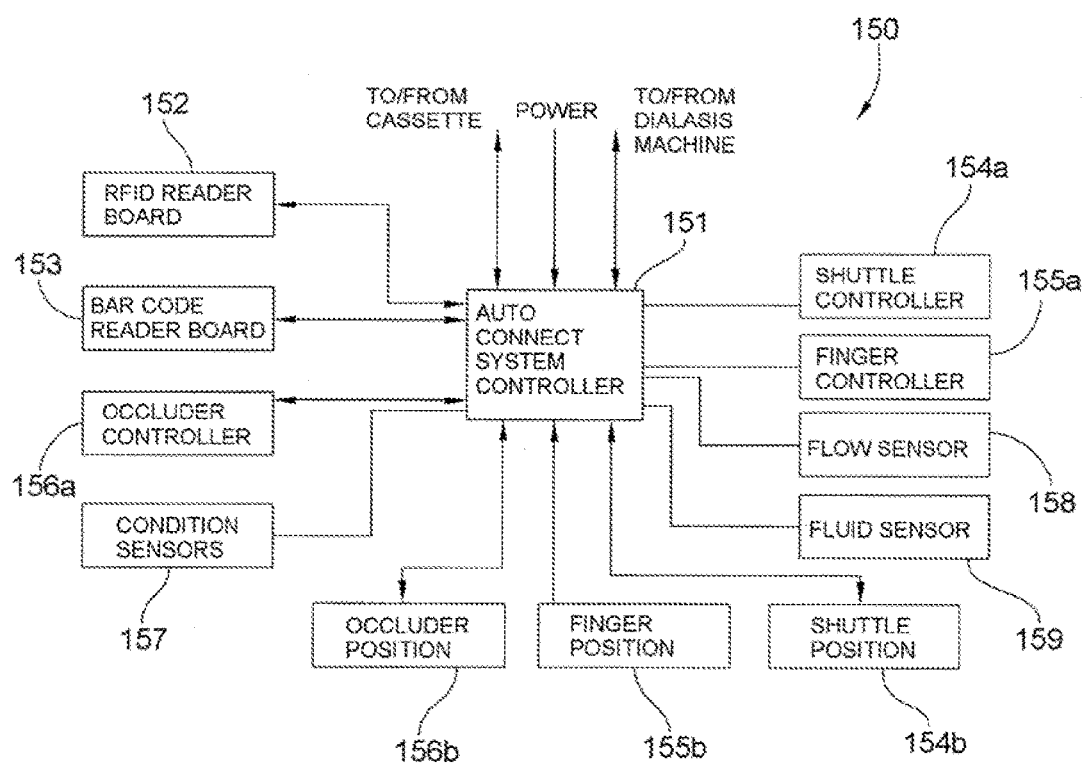

The control systems for operating the autoconnect and the associated equipment are also disclosed in FIGS. 22 and 23. The control system 140 for the dialysis machine, the disposable cassette, and the autoconnect device are depicted in FIG. 22. The patient autoconnect controller 143 is in communication with the disposable cassette controller 142 with an external interface. The autoconnect controller 143 is in communication with the dialysis machine controller 141 via an external patient autoconnect interface. Dialysis machine controller 141 includes a microcontroller 141a and a memory 141b for storing a computer program for operating the controller 141. The individual containers or bags of dialysis solution 144 are supplied with unique identifiers and when these identifiers are read, the containers may be said to interface with the dialysis machine controller 141, the disposable cassette controller 142, or as noted above, the autoconnect controller 143. The system controllers may also have other interfaces and connections. As noted above, the unique identifiers may be read in many ways, for example, by a camera 145 operably connected to the dialysis machine controller.

The term camera as used here also includes related optical devices capable of reading such a mark, including but not limited to, a visible/IR camera, a charge-coupled device (CCD), a CMOS image sensor or camera, an optical sensor, or other suitable device. Cameras for imaging in visible light are readily available. Cameras that capture infrared (heat) images are also available. Recently, cameras that can produce composite images using visible and infrared radiation are now available, such as those from Fluke Thermography and Fluke Corp., Everett, Wash., USA. Images that include an indication of temperature may also assist in the sense of letting users know when and if the containers have been warmed, for instance to body temperature. The camera may also be used to verify that the connectors are undamaged and that they are correctly loaded into the shuttle or other portion of the autoconnect device. If the connectors are damaged or the markings are inconsistent with the expected markings for the containers, the machine controller for the dialysis system or for the autoconnect device may signal an alarm or refuse to proceed. In one embodiment, the camera may also be used to inspect the color or other readily-determined optical property of the contents of the containers, and if the inspection of the color or other property does not yield the expected result, the system may signal an alarm or refuse to proceed.

The autoconnect control system 150 is depicted in FIG. 23. The autoconnect system is controlled by a microcontroller 151. A great many microcontrollers, and microprocessor controllers, are suitable for this application. Indeed, even application specific integrated controllers (ASICs) may be used. We have found that microcontrollers from STMicroelectronics, Austin, Tex., work well. Other microcontrollers that will be satisfactory include those from Freescale Corp., Austin, Tex., or Atmel Corp., San Jose, Calif. Other suitable microcontrollers may also be used.

System controller 151 is in communication with a great many other devices and parts of the autoconnect system, as discussed above. System controller 151 is in communication with RFID reader board 152, bar code reader board 153, if supplied, shuttle controller 154a, shuttle position sensor 154b, finger controller 155a, and finger position sensors 155b. In addition, the system controller 151 is in communication and control with the occluder controller 156a and the occluder position sensors 156b. In some systems, only a single occluder is used.

In addition, a number of additional sensors 157 are used in embodiments of the autoconnect system. For example, temperature sensors may be used near the tubing or the shuttle channels to detect a temperature related to the dialysis fluid or other liquid that is being auto-connected. Temperature sensors may also be used near the shuttle lead screws or other transport to insure that overheating is not occurring. If pneumatic cylinders or air solenoids are used, at least one or two pressure sensors should be used to keep a check on the health of the inlet air or air pump outlet that is used to supply air pressure. If hydraulic fluid is used, pressure sensors should be used to monitor and regulate hydraulic fluid pressure in the system.

It is also desirable to include a flow sensor 158. For example, a non-contacting optical flow sensor may be used to detect flow of dialysis fluid within the tubing, based on minute changes in reflection or refraction of the fluid within the tubing. A single pressure sensor of a two-port delta-p pressure sensor may be used along the tubing to detect flow by the change in pressure, or pressure drop, between the ports. Actual rotating, contact-type flow sensors may also be used. Finally, it may also be prudent to add a fluid sensor 159 for measuring specific properties of the solution, such as pH or conductivity. The fluid sensor is preferably placed directly in the flow stream for accurate measurement of the appropriate property.

Figure 24:
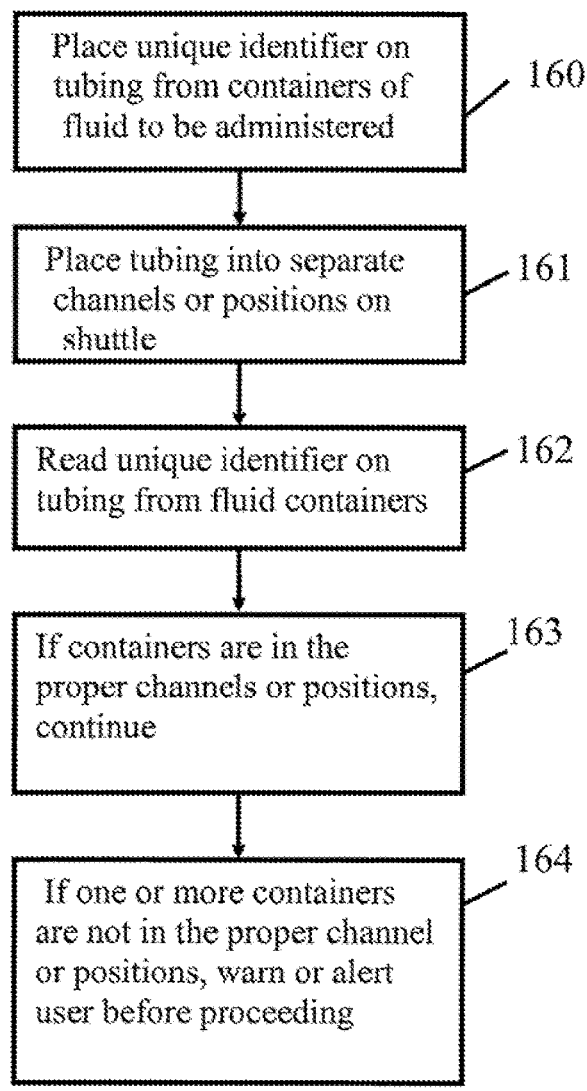
FIGS. 24-25 are flowcharts for methods of operating autoconnect devices.
Figure 25:
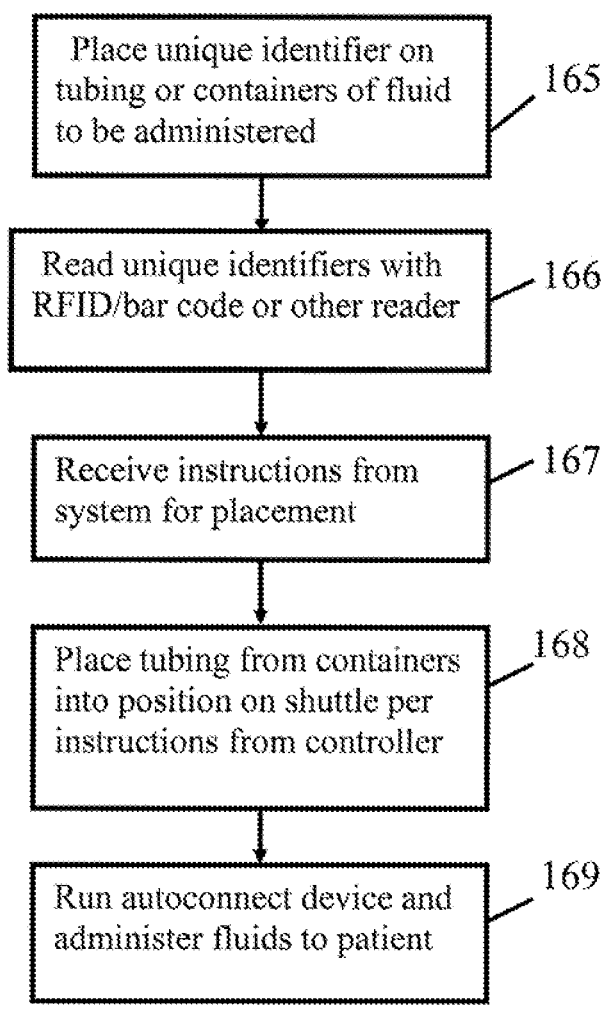

FIGS. 24-25 are flowcharts depicting how the automatic identification features of the autoconnect device operate in different embodiments. In one embodiment, depicted in FIG. 24, there is an RFID reader in each channel or position on the shuttle. There is also an RFID tag on the tubing from each container of fluid, such as dialysate fluid. The user places 160 an RFID tag with a unique identifier on tubing from the fluid container that contains the fluid to be administered to a patient. The tubing and RFID tag is then placed 161 into separate channels or positions on the shuttle. The reader in each position then reads 162 the RFID tag on the tubing from one or more containers. If the computer recognizes that the RFID tags corresponding to the containers are in the proper place, the operation continues 163. If one or more containers are not in the proper position, an alert or alarm is issued 164 to the user before proceeding.

In another embodiment, depicted in FIG. 25, there is only a single RFID reader or bar code reader operably connected to the autoconnect device. In this embodiment, the unique identifier for each container of fluid may be located 165 on tubing or on the container or bag itself. The user, using the bar code reader or RFID reader, then reads 166 the unique identifiers on each container or tubing, the unique identifiers being an RFID chip or bar code indicia or label. The computer and computer program receives the information about the containers and then instructs 167 the user concerning the position to place the tubing for each of the containers. The user then places 168 the tubing from the containers into the instructed position on the shuttle in accordance with the instructions. The user then operates 169 the autoconnect device and administers fluids to the patient.

It should be understood that various changes and modifications to the presently preferred embodiments described herein will be apparent to those having skill in the art. For instance, the autoconnect machine may be used with pumping cassettes used in peritoneal dialysis machines. Embodiments of autoconnect machines may also be used for cassettes for hemodialysis systems, automated peritoneal dialysis, and continuous flow peritoneal dialysis systems. These cassettes may employ any suitable pump or other fluid transfer mechanism, used with the autoconnect machine. Such changes and modifications can be made without departing from the spirit and scope of the present disclosure and without diminishing its intended advantages. Such changes and modifications are included in the appended claims.

The invention is claimed as follows:

1. A dialysis system comprising:
 a disposable fluid pumping cassette including at least one flexible membrane attached to a housing and at least one port extending from the housing, the at least one port including a spike;
 at least one dialysis fluid supply in fluid communication with at least one tubing and tubing connector;
 an autoconnection device including a shuttle for moving the at least one tubing and tubing connector towards the spike of the at least one port, the autoconnection device including at least one lead screw in mechanical communication with the shuttle, a motor and power transmission equipment to transmit power from the motor to the at least one lead screw; and
 a controller programmed to operate the motor to move the at least one tubing and tubing connector towards the spike of the at least one port of the disposable fluid pumping cassette.

2. The dialysis system of claim 1, wherein the power transmission equipment is configured to operate with the motor to produce a desired speed for moving the shuttle.

3. The dialysis system of claim 2, wherein the power transmission equipment includes a timing belt in mechanical communication with the motor to produce the desired speed for moving the shuttle.

4. The dialysis system of claim 2, wherein the power transmission equipment includes a gear reduction in mechanical communication with the motor to produce the desired speed for moving the shuttle.

5. The dialysis system of claim 1, wherein the lead screw is in threaded communication with the shuttle.

6. The dialysis system of claim 1, which includes two lead screws in mechanical communication with opposing ends of the shuttle.

7. The dialysis system of claim 1, wherein the shuttle grasps the at least one tubing and tubing connector.

8. The dialysis system of claim 1, wherein the shuttle includes at least one channel for accepting the at least one tubing and tubing connector.

9. The dialysis system of claim 1, wherein the shuttle includes at least one occluder for occluding the at least one tubing.

10. The dialysis system of claim 1, which includes a sensor operating with the controller to operate the motor to move the at least one tubing and tubing connector towards the spike of the at least one port in a desired manner.

11. The dialysis system of claim 9, wherein the sensor is an optical sensor.

12. The dialysis system of claim 9, wherein the sensor is mounted to and moves with the shuttle.

13. The dialysis system of claim 1, wherein the controller is programmed to operate the motor to move the at least one tubing and tubing connector towards and away from the spike of the at least one port of the disposable fluid pumping cassette.

14. The dialysis system of claim 1, wherein the at least one connector is provided with a cap, and wherein the controller is programmed to operate the motor to move the at least one tubing and tubing connector (i) away from the disposable fluid pumping cassette to remove the cap from the connector and (ii) towards the disposable fluid pumping cassette to cause the spike to spike the connector.

15. The dialysis system of claim 14, wherein the at least one port is provided with a cap, and wherein the controller is further programmed between (i) and (ii) to (iii) cause a finger to be rotated to remove the cap from the at least one port.

16. The dialysis system of claim 1, wherein the at least one lead screw is a ballscrew that operates using ball bearings.

* * * * *